United States Patent
Clark et al.

(10) Patent No.: US 12,414,826 B2
(45) Date of Patent: *Sep. 16, 2025

(54) SYSTEMS AND METHODS FOR A CONTROL STATION FOR ROBOTIC INTERVENTIONAL PROCEDURES USING A PLURALITY OF ELONGATED MEDICAL DEVICES

(71) Applicant: Corindus, Inc., Newton, MA (US)

(72) Inventors: Andrew Clark, Arlington, MA (US); Eric Klem, Lexington, MA (US); Omid Saber, Waltham, MA (US); Saeed Sokhanvar, Belmont, MA (US); Per Bergman, West Roxbury, MA (US); Cameron Canale, Groton, MA (US); Steven J. Blacker, Framingham, MA (US); Dino Kasvikis, Barrington, RI (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 65 days.

This patent is subject to a terminal disclaimer.

(21) Appl. No.: 18/405,067

(22) Filed: Jan. 5, 2024

(65) Prior Publication Data
US 2024/0173085 A1 May 30, 2024

Related U.S. Application Data

(63) Continuation of application No. 17/597,411, filed as application No. PCT/US2020/041985 on Jul. 14, 2020, now Pat. No. 11,896,325.
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/25* (2016.02); *A61B 34/74* (2016.02); *B25J 13/065* (2013.01);
(Continued)

(58) Field of Classification Search
CPC .......................... A61B 34/25; A61B 2034/742
See application file for complete search history.

(56) References Cited

U.S. PATENT DOCUMENTS 3,821,525 A   6/1974 Eaton et al.
3,922,996 A   12/1975 Meyer
(Continued)

FOREIGN PATENT DOCUMENTS

CN   101427205   5/2009
CN   102124425   7/2011
(Continued)

OTHER PUBLICATIONS

Sato et al., Touche': Enhancing Tough Interaction on Humans, Screens, Liquids, and Everyday Objects, CHI' 12, May 5-10, 2012, Austin, Texas, USA, Copyright 2012 ACM 978-1-4503-1015-4/12/05, 10 pages.
(Continued)

*Primary Examiner* — Scott Luan

(57) ABSTRACT

A system for controlling a catheter-based procedure system that includes a robotic drive configured to control rotational motion and axial motion of one or more elongated medical devices may include a body, a first control coupled to the body, and a second control coupled to the body. First control is configured to instruct the robotic drive to axially move one of the one or more elongated medical devices in response to
(Continued)

manipulation of the first control by a user, and the second control is configured to instruct the robotic drive to rotate one of the one or more elongated medical devices in response to manipulation of the second control by the user, wherein the first control and the second control are positioned on the body so the first control and the second control can be simultaneously manipulated by a first digit and a second digit on a hand of the user.

20 Claims, 15 Drawing Sheets

Related U.S. Application Data

(60) Provisional application No. 62/874,282, filed on Jul. 15, 2019.

(51) Int. Cl.
  A61B 34/20 (2016.01)
  A61B 90/00 (2016.01)
  B25J 13/06 (2006.01)
  G05G 1/01 (2008.04)

(52) U.S. Cl.
  CPC ........ *G05G 1/01* (2013.01); *A61B 2034/2059* (2016.02); *A61B 2034/301* (2016.02); *A61B 2034/742* (2016.02); *A61B 2090/064* (2016.02); *A61B 2090/376* (2016.02)

(56) References Cited

U.S. PATENT DOCUMENTS

| | | | |
|---|---|---|---|
| 4,706,671 A | 11/1987 | Weinrib | |
| 4,926,858 A | 5/1990 | Gifford et al. | |
| 5,217,474 A | 6/1993 | Zacca et al. | |
| 5,312,338 A | 5/1994 | Nelson et al. | |
| 5,350,101 A | 9/1994 | Godlewski | |
| 5,527,279 A | 6/1996 | Imran | |
| 5,854,622 A | 12/1998 | Brannon | |
| 5,907,487 A | 5/1999 | Rosenberg et al. | |
| 6,590,171 B1 | 7/2003 | Wolf et al. | |
| 7,331,967 B2 | 2/2008 | Lee et al. | |
| 7,557,797 B2 | 7/2009 | Ludwig | |
| 7,766,856 B2 | 8/2010 | Ferry et al. | |
| 7,766,894 B2 | 8/2010 | Weitzner et al. | |
| 7,972,298 B2 | 7/2011 | Wallace et al. | |
| 8,052,636 B2 | 11/2011 | Moll et al. | |
| 8,092,397 B2 | 1/2012 | Wallace et al. | |
| 8,343,096 B2 | 1/2013 | Kirschenman et al. | |
| 8,390,438 B2 | 3/2013 | Olson et al. | |
| 8,617,102 B2 | 12/2013 | Moll et al. | |
| 8,684,952 B2 | 4/2014 | Weitzner et al. | |
| 8,736,212 B2 | 5/2014 | Sandhu et al. | |
| 8,801,661 B2 | 8/2014 | Moll et al. | |
| 9,198,714 B2 | 12/2015 | Worrell et al. | |
| 9,220,568 B2 | 12/2015 | Bromander et al. | |
| 9,283,046 B2 | 3/2016 | Walker et al. | |
| 9,320,479 B2 | 4/2016 | Wenderow et al. | |
| 9,326,822 B2 | 5/2016 | Lewis et al. | |
| 9,408,669 B2 | 8/2016 | Kokish et al. | |
| 9,566,414 B2 | 2/2017 | Wong et al. | |
| 9,655,680 B2 | 5/2017 | Shim et al. | |
| 9,713,500 B2 | 7/2017 | Kim et al. | |
| 9,770,300 B2 | 9/2017 | Kwon et al. | |
| 9,782,564 B2 | 10/2017 | Zirps et al. | |
| 9,814,864 B2 | 11/2017 | Scarpine et al. | |
| 9,825,455 B2 | 11/2017 | Sandhu et al. | |
| 10,213,264 B2 | 2/2019 | Tanner et al. | |
| 10,238,456 B2 | 3/2019 | Murphy et al. | |
| 10,307,214 B2 | 6/2019 | Lathrop et al. | |
| 10,599,233 B1 | 3/2020 | AMalou | |
| 2002/0177789 A1 | 11/2002 | Ferry et al. | |
| 2004/0011154 A1 | 1/2004 | Dybro | |
| 2004/0147934 A1 | 7/2004 | Kiester | |
| 2004/0254566 A1 | 12/2004 | Plicchi et al. | |
| 2005/0119615 A1 | 6/2005 | Noriega et al. | |
| 2006/0074442 A1 | 4/2006 | Noriega et al. | |
| 2006/0243080 A1 | 11/2006 | Takamoto et al. | |
| 2007/0060879 A1 | 3/2007 | Weitzner et al. | |
| 2008/0161801 A1 | 7/2008 | Steinke et al. | |
| 2008/0243064 A1 | 10/2008 | Stahler et al. | |
| 2008/0255704 A1 | 10/2008 | Braut | |
| 2009/0082722 A1 | 3/2009 | Munger et al. | |
| 2009/0213073 A1 | 8/2009 | Obermeyer et al. | |
| 2009/0248042 A1 | 10/2009 | Kirschenman | |
| 2010/0010505 A1 | 1/2010 | Herlihy et al. | |
| 2010/0073150 A1 | 3/2010 | Olson | |
| 2010/0175701 A1 | 7/2010 | Reis et al. | |
| 2010/0274087 A1 | 10/2010 | Diolaiti et al. | |
| 2011/0237880 A1 | 9/2011 | Hamel et al. | |
| 2012/0001860 A1 | 1/2012 | Phan Le | |
| 2012/0071752 A1 | 3/2012 | Sewell et al. | |
| 2013/0172906 A1 | 7/2013 | Olson et al. | |
| 2014/0194897 A1 | 7/2014 | Kirschenman et al. | |
| 2014/0276389 A1 | 9/2014 | Walker | |
| 2014/0276646 A1 | 9/2014 | Wong et al. | |
| 2014/0277002 A1 | 9/2014 | Grace | |
| 2014/0277333 A1 | 9/2014 | Lewis et al. | |
| 2014/0277747 A1 | 9/2014 | Walker et al. | |
| 2015/0142013 A1 | 5/2015 | Tanner et al. | |
| 2015/0157497 A1 | 6/2015 | Hufford et al. | |
| 2015/0245876 A1 | 9/2015 | Kim et al. | |
| 2015/0265807 A1 | 9/2015 | Park | |
| 2016/0270780 A1 | 9/2016 | Hall et al. | |
| 2016/0346048 A1 | 12/2016 | Wenderow et al. | |
| 2017/0007343 A1 | 1/2017 | Yu | |
| 2017/0348060 A1 | 12/2017 | Blacker | |
| 2017/0367773 A1 | 12/2017 | Kottenstette et al. | |
| 2018/0325612 A1 | 11/2018 | Blacker et al. | |
| 2019/0105110 A1 | 4/2019 | Tanner et al. | |
| 2019/0175062 A1 | 6/2019 | Rafii-Tari et al. | |
| 2019/0175887 A1 | 6/2019 | Shameli | |
| 2020/0078104 A1 | 3/2020 | Bailey et al. | |
| 2020/0289228 A1 | 9/2020 | Denlinger et al. | |
| 2020/0397531 A1 | 12/2020 | Schrader et al. | |

FOREIGN PATENT DOCUMENTS

| | | |
|---|---|---|
| CN | 102292692 | 12/2011 |
| EP | 0974889 | 1/2000 |
| EP | 1779801 | 5/2007 |
| EP | 2124800 | 11/2010 |
| EP | 2266473 | 12/2010 |
| EP | 2923669 | 6/2017 |
| JP | 2008515135 | 5/2008 |
| JP | 2006253000 | 2/2015 |
| JP | 2015037572 | 2/2015 |
| WO | 0161431 | 8/2001 |
| WO | 2003015428 | 12/2003 |
| WO | 2007005976 | 1/2007 |
| WO | 2007008967 | 1/2007 |
| WO | 2010025338 | 3/2010 |
| WO | 2010078344 | 7/2010 |
| WO | 2011046874 | 4/2011 |
| WO | 2011094877 | 8/2011 |
| WO | 2012129374 | 9/2012 |
| WO | 2017060439 | 4/2017 |
| WO | 2018005680 | 1/2018 |
| WO | 2019027922 | 2/2019 |

OTHER PUBLICATIONS

Rafael Beyar, et al: "Remote-Control Percutaneous Coronary Interventions," Concept, Validation, and First-in-Humans Pilot Clinical Trial, Journal of the Amercian College of Cardiology, vol. 47, No. 2, 2006, pp. 296-300.
European Search Report for Corresponding Application No. EP 20840218.0, dated Dec. 9, 2022.
European Search Report for Corresponding Application No. EP 20840218.0, dated Aug. 8, 2022.

(56) References Cited

OTHER PUBLICATIONS

"Joystick Control Teleoperation," Robot Operating System (ROS), May 15, 2018 (from edit history), available at https://rosplanning.github.io/moveit_tutorials/doc/joystick_control_teleoperation/joystick_control_teleoperation_tutorial.html (Year: 2018).
Frank ("Nintendo Switch one-handed Joy-Con adapter opens up the console to everyone," Aug. 17, 2017 (Year: 2017).
International Search Report Received for Corresponding PCT Application No. PCT/US2020/041985, dated Oct. 1, 2020.
Auris Health, Inc. (2018), MONARCH Platform: User Manual.

SYSTEMS AND METHODS FOR A CONTROL STATION FOR ROBOTIC INTERVENTIONAL PROCEDURES USING A PLURALITY OF ELONGATED MEDICAL DEVICES

CROSS-REFERENCE TO RELATED APPLICATIONS

This application is a continuation of U.S. patent application Ser. No. 17/597,411, filed Jan. 5, 2022, which is a National Phase application of PCT Application No. PCT/US2020/041985, filed Jul. 14, 2020, which claims priority to U.S. Provisional Patent Application No. 62/874,282, filed Jul. 15, 2019, the contents of which are incorporated by reference herein for all purposes.

FIELD

Embodiments of an input system can be configured to control a catheter-based procedure system in a variety of different modes that use various combinations of input controls as motion and/or selection controls. When used as a motion control, an input control can be configured to control axial and/or rotational movement of at least one elongated medical device. Further, input controls that are used as motion controls may be configured to control movement of an elongated medical device in a position control mode or a speed control mode.

Embodiments relate generally to the field of robotic medical procedure systems and, in particular, to systems, apparatus and methods for robotically controlling the movement and operation of one or more elongated medical devices in robotic interventional procedures.

BACKGROUND

As used herein, the term elongated medical device (EMD) refers to, but is not limited to, catheters (e.g., guide catheters, microcatheters, balloon/stent catheters), wire-based devices (e.g., guidewires, embolization coils, stent retrievers, etc.), and medical devices comprising any combination of these. The term wire-based EMD includes but is not limited to guidewires, microwires, a proximal pusher for embolization coils, stent retrievers, self-expanding stents, and flow diverters. Typically wire-based EMDs do not have a hub or handle at their proximal terminal end.

In one embodiment the EMD is a catheter having a hub at a proximal end of the catheter and a flexible shaft extending from the hub toward the distal end of the catheter, wherein the shaft is more flexible than the hub. In one embodiment the catheter includes an intermediary portion that transitions between the hub and the shaft that has an intermediate flexibility that is less rigid than the hub and more rigid than the shaft. In one embodiment the intermediary portion is a strain relief.

The term drive module refers to the combination of a device module and a cassette.

The term cassette generally refers to the part (non-capital, consumable or sterilizable unit) of the robotic drive system that normally is the sterile interface between a device module and at least one EMD (directly) or through a device adapter (indirectly).

The term device module generally refers to the part (e.g., the capital part) of the robotic drive system that normally contains one or more motors with drive couplers that interface with the cassette.

The term front refers to the side of the robotic drive that faces a bedside user and away from the positioning system, such as the articulating arm. The term rear refers to the side of the robotic drive that is closest to the positioning system, such as the articulating arm.

The term inwardly refers to the inner portion of a feature. The term outwardly refers to the outer portion of a feature.

The terms top, up, and upper refer to the general direction away from the direction of gravity and the terms bottom, down, and lower refer to the general direction in the direction of gravity.

The terms user or operator refer to a user or operator at a control station. The terms also refer to as a control station user or control station operator.

The terms bedside user or bedside operator refer to a user or operator at a bedside unit.

The term local is used to refer to the location of the patient and bedside unit. For example, a local site is the location of the bedside unit and a patient or subject. At a local site, a user or operator and a control station may be located in the same room or an adjacent room to the patient and bedside unit.

The term remote is used to refer to locations that do not have physical access to the bedside unit and/or patient at a local site. For example, a remote site is a location of a user or operator and a control station used to control the bedside unit remotely. A remote location and a local location are away from one another, for example, in different rooms in the same building, different buildings in the same city, different cities, etc.

The term longitudinal axis of a member (for example, an EMD or other element in the catheter-based procedure system) is the line or axis along the length of the member that passes through the center of the transverse cross section of the member in the direction from a proximal portion of the member to a distal portion of the member. For example, the longitudinal axis of a guidewire is the central axis in the direction from a proximal portion of the guidewire toward a distal portion of the guidewire even though the guidewire may be non-linear in the relevant portion.

The term axial movement of a member refers to translation of the member along the longitudinal axis of the member. For example, when the distal end of an EMD is axially moved in a distal direction along its longitudinal axis into or further into the patient, the EMD is being advanced. When the distal end of an EMD is axially moved in a proximal direction along its longitudinal axis out of or further out of the patient, the EMD is being withdrawn.

The term axial insertion refers to inserting a first member into a second member along the longitudinal axis of the second member. For example, an EMD that is axially loaded in a collet is axially inserted in the collet. An example of axial insertion could be referred to as back loading a catheter on the proximal end of a guidewire.

The term lateral insertion refers to inserting a first member into a second member along a direction in a plane perpendicular to the longitudinal axis of the second member. This can also be referred to as radial loading or side loading.

The term rotational movement of a member refers to the change in angular orientation of the member about the local longitudinal axis of the member. For example, rotational movement of an EMD corresponds to clockwise or counterclockwise rotation of the EMD about its longitudinal axis due to an applied torque.

The term continuous motion refers to motion that does not require a reset and is uninterrupted.

The term discrete motion refers to motion that requires a reset and is interrupted.

The terms distal and proximal define relative locations of two different features. With respect to a robotic drive the terms distal and proximal are defined by the position of the robotic drive in its intended use relative to a patient.

When used to define a relative position, the distal feature is the feature of the robotic drive that is closer to the patient than a proximal feature when the robotic drive is in its intended in-use position. Within a patient, any vasculature landmark further away along the path from the access point is considered more distal than a landmark closer to the access point, where the access point is the point at which the EMD enters the patient.

Similarly, the proximal feature is the feature that is farther from the patient than the distal feature when the robotic drive in its intended in-use position.

When used to define direction, the distal direction refers to a path on which something is moving or is aimed to move or along which something is pointing or facing from a proximal feature toward a distal feature and/or patient when the robotic drive is in its intended in-use position. The proximal direction is the opposite direction of the distal direction. For example, referring to FIG. 1, a robotic device is shown from the viewpoint of an operator facing a patient. In this arrangement, the distal direction is along the positive X coordinate axis and the proximal direction is along the negative X coordinate axis.

With respect to movement of the individual modules, and referring to FIG. 3, the EMD is moved in a distal direction on a path toward a patient through the introducer interface support 74 which defines the distal end of the robotic drive 24. The proximal end of the robotic drive 24 is the point furthest from the distal end along the negative X axis.

With respect to positions of the individual modules, and referring to FIG. 3, the most distal device module is the device module 32a closest to the distal end of the robotic drive 24. The most proximal device module is the device module 32d positioned furthest from the distal end of the robotic drive 24 along the negative X axis. The relative position of device modules is determined by their relative location to the distal end of the robotic drive. For example, device module 32b is distal to device module 32c.

With respect to distal/proximal portions, sections or ends of an EMD or the robotic drive, and referring to FIG. 3, the portions of cassette 66a and device module 68a are defined by their relative location to the distal end of the robotic drive. For example, the distal end of cassette 66a is the portion of the cassette that is closest to the distal end of the robotic drive and the proximal end of cassette 66a is the portion of the cassette that is furthest from the distal end of the robotic drive along the negative X axis when the cassette is in-use position on device module 68a. Stated in another way, the distal end of cassette 66a is the portion of the cassette through which an EMD is closest to the path leading to a patient in the in-use position.

The term force refers to an agent which causes or tends to cause motion of a body. A force acting on a body may change the motion of the body, retard the motion of the body, balance the forces already acting on the body, and give rise to internal stresses in the body. Characteristics of a force include the magnitude of the force, the line of action of the force (the axis along which the force acts), the direction of the force (corresponding to compressive or tensile force), and the point at which the force is acting.

The term load refers to forces, torques, or combination of forces and torques. The load may include a single component of force (a force along a single axis) or multiple components of forces (multi-axial forces) and/or a single component of torque (a torque around a single axis) or multiple components of torque (multi-axial torque). The load may be static (not change with time) or dynamic (change with time).

The term load sensor refers to a sensor that measures one or more components of force and/or torque. For example, a uniaxial load sensor measures force along one axis or torque about one axis. A multiaxial load sensor measures force and/or torque in multiple mutually orthogonal axes. A load sensor generally generates electrical signals in response to load (for example, a strain gauge based load sensor generates charge in response to load) and generally requires signal conditioning circuitry to convert the signals to force and/or torque. As such, a load sensor is a transducer that converts one or more components of compressive and/or tensile force and/or clockwise and/or counterclockwise torque into a measurable electrical output (for example, voltage or current).

Catheters and other elongated medical devices (EMDs) may be used for minimally invasive medical procedures for the diagnosis and treatment of diseases of various vascular systems, including neurovascular intervention (NVI) also known as neurointerventional surgery, percutaneous coronary intervention (PCI) and peripheral vascular intervention (PVI). These procedures typically involve navigating a guidewire through the vasculature, and via the guidewire advancing a catheter to deliver therapy. The catheterization procedure starts by gaining access into the appropriate vessel, such as an artery or vein, with an introducer sheath using standard percutaneous techniques. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire.

The physician or operator may use an imaging system (e.g., fluoroscope) to obtain a cine with a contrast injection and select a fixed frame for use as a roadmap to navigate the guidewire or catheter to the target location, for example, a lesion. Contrast-enhanced images are also obtained while the physician delivers the guidewire or catheter so that the physician can verify that the device is moving along the correct path to the target location. While observing the anatomy using fluoroscopy, the physician manipulates the proximal end of the guidewire or catheter to direct the distal tip into the appropriate vessels toward the lesion or target anatomical location and avoid advancing into side branches.

Robotic catheter-based procedure systems have been developed that may be used to aid a physician in performing catheterization procedures such as, for example, NVI, PCI and PVI. Examples of NVI procedures include coil embolization of aneurysms, liquid embolization of arteriovenous malformations and mechanical thrombectomy of large vessel occlusions in the setting of acute ischemic stroke. In an NVI procedure, the physician uses a robotic system to gain target lesion access by controlling the manipulation of a neurovascular guidewire and microcatheter to deliver the therapy to restore normal blood flow. Target access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several embolization coils are deployed into the aneurysm through the microcatheter and used to block blood flow into the aneurysm. For treating arteriovenous malformations, a liquid embolic is injected into the malformation via a microcatheter. Mechanical thrombectomy to treat vessel occlusions can be achieved either through aspiration and/or use of a stent retriever. Depending on the location of the clot, aspiration is either done through an aspiration catheter, or through a microcatheter for smaller arteries. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter (or intermediate catheter) into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or fractional flow reserve (FFR) measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

When support at the distal end of a catheter or guidewire is needed, for example, to navigate tortuous or calcified vasculature, to reach distal anatomical locations, or to cross hard lesions, an over-the-wire (OTW) catheter or coaxial system is used. An OTW catheter has a lumen for the guidewire that extends the full length of the catheter. This provides a relatively stable system because the guidewire is supported along the whole length. This system, however, has some disadvantages, including higher friction, and longer overall length compared to rapid-exchange catheters (see below). Typically to remove or exchange an OTW catheter while maintaining the position of the indwelling guidewire, the exposed length (outside of the patient) of guidewire must be longer than the OTW catheter. A 300 cm long guidewire is typically sufficient for this purpose and is often referred to as an exchange length guidewire. Due to the length of the guidewire, two operators are needed to remove or exchange an OTW catheter. This becomes even more challenging if a triple coaxial, known in the art as a tri-axial system, is used (quadruple coaxial catheters have also been known to be used). However, due to its stability, an OTW system is often used in NVI and PVI procedures. On the other hand, PCI procedures often use rapid exchange (or monorail) catheters.

The guidewire lumen in a rapid exchange catheter runs only through a distal section of the catheter, called the monorail or rapid exchange (RX) section. With a RX system, the operator manipulates the interventional devices parallel to each other (as opposed to with an OTW system, in which the devices are manipulated in a serial configuration), and the exposed length of guidewire only needs to be slightly longer than the RX section of the catheter. A rapid exchange length guidewire is typically 180-200 cm long. Given the shorter length guidewire and monorail, RX catheters can be exchanged by a single operator. However, RX catheters are often inadequate when more distal support is needed.

When performing vascular interventional procedures, the operator generally uses a set of controls provided at a control station in order to control the robotic system to move each catheter or wire. Each of the controls is typically configured to a control a specific device, or to move the catheter or wire in a specific manner. Thus, it is sometimes necessary for the operator to switch between different controls or operate multiple controls simultaneously.

SUMMARY

In accordance with an embodiment, an input system can be configured for controlling a catheter-based procedure system. The catheter-based procedure system can include a robotic drive that may be configured to control rotational motion and axial motion of one or more elongated medical devices. The input system can include a body, a first control, and a second control. The first control can be configured to instruct the robotic drive to axially move one of the one or more elongated medical devices in response to manipulation of the first control by a user, and the second control can be configured to instruct the robotic drive to rotate one of the one or more elongated medical devices in response to manipulation of the second control by the user. The first control and the second control may be positioned on the body so that the first control and the second control can be simultaneously manipulated by a first digit and a second digit on a hand of the user.

In accordance with another embodiment, an input system can be configured for controlling a catheter-based procedure system. The catheter-based procedure system may include a robotic drive that may be configured to control movement of a first elongated medical device and a second elongated medical device. The input system can include a handheld body, a first control, and a second control. The first control can be configured to instruct the robotic drive to move the first elongated medical device in response to manipulation of the first control by a user. The second control can be configured to instruct the robotic drive to move the second elongated medical device in response to manipulation of the second control by the user. Instruction of the robotic drive to move the first elongated medical device may occur simultaneously with instruction of the robotic drive to move the second elongated medical device In accordance with another embodiment, an input system can be configured for controlling a catheter-based procedure system. The catheter-based procedure system can include a robotic drive that may be configured to control movement of an elongated medical device. The input system can include a first control and a second control. The first control can be configured to instruct the robotic drive to move the elongated medical device a discrete amount in a first degree of freedom in response to activation of the first control by a user. The second control can be configured to instruct the robotic drive to continuously move the elongated medical device in the first degree of freedom in response to activation of the second control by the user.

In accordance with another embodiment, a method for an input system for controlling a catheter-based procedure system that includes a robotic drive configured to control rotational motion and axial motion of one or more elongated medical devices includes receiving a first manipulation by a first digit of a first hand of a user of a first control coupled to a body of the input system, receiving a second manipulation by a second digit of the first hand of the user of a second control coupled to the body of the input system, instructing, responsive to the first manipulation, the robotic drive to axially move one of the one or more elongated medical devices, and, responsive to the second manipulation, instructing the robotic drive to rotate one of the one or more elongated medical devices, wherein the first manipulation and the second manipulation occur simultaneously.

In accordance with another embodiment, a method for an input system for controlling a catheter-based procedure system that includes a robotic drive configured to control movement of a first elongated medical device and a second elongated medical device includes receiving a first manipulation of a first control coupled to a handheld body of the input system, receiving a second manipulation of a second control coupled to the handheld body of the input system, instructing, responsive to the first manipulation, the robotic drive to move the first elongated medical device, and, responsive to the second manipulation, instructing the robotic drive to move the second elongated medical device, wherein the first manipulation and the second manipulation occur simultaneously.

BRIEF DESCRIPTION OF THE DRAWINGS

Embodiments will become more fully understood from the following detailed description, taken in conjunction with the accompanying drawings, wherein the reference numerals refer to like parts in which.

DETAILED DESCRIPTION

Figure 1:
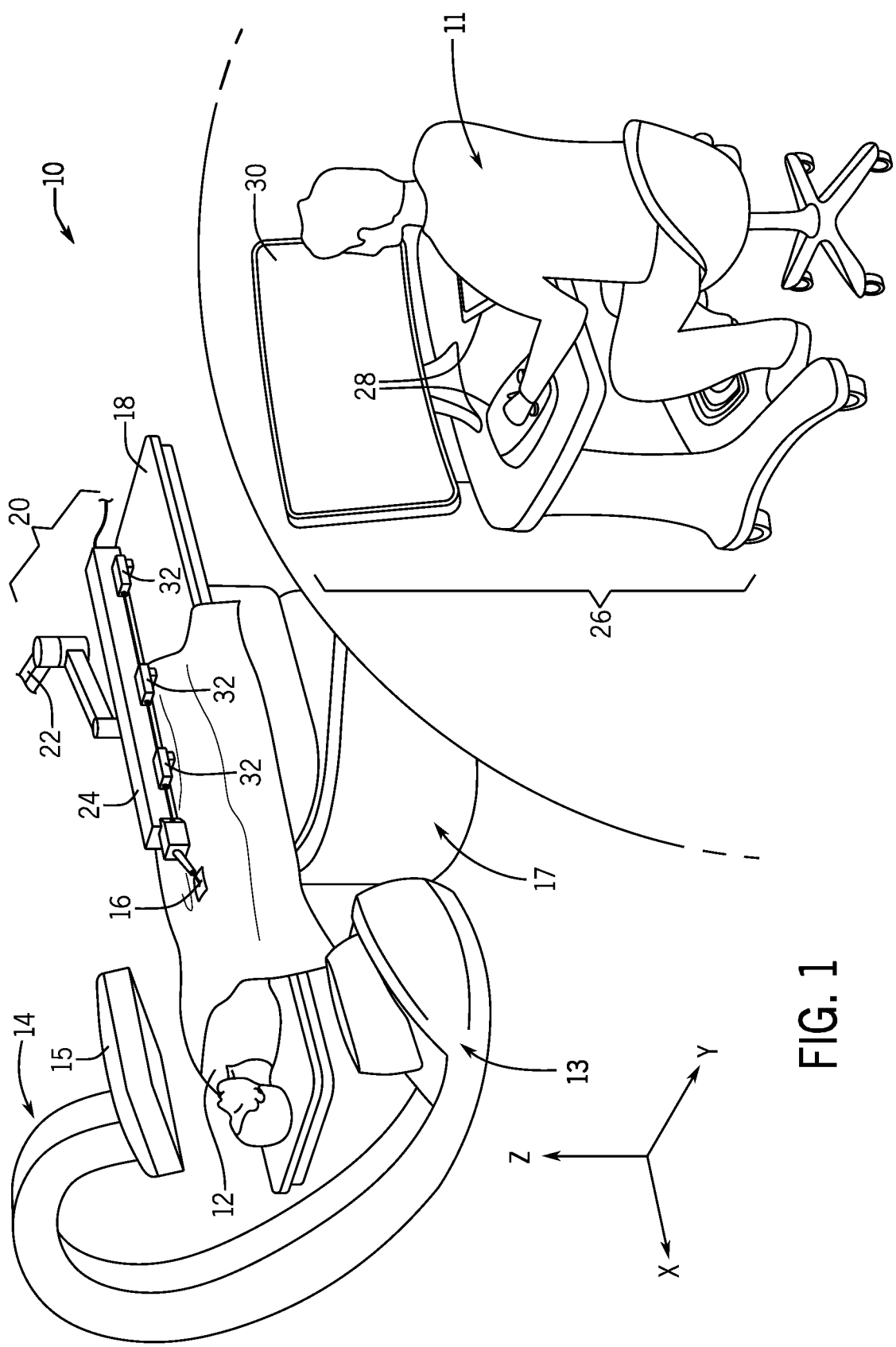
FIG. 1 is a perspective view of an exemplary catheter-based procedure system in accordance with an embodiment.

FIG. 1 is a perspective view of an exemplary catheter-based procedure system 10 in accordance with an embodiment. Catheter-based procedure system 10 may be used to perform catheter-based medical procedures, e.g., percutaneous intervention procedures such as a percutaneous coronary intervention (PCI) (e.g., to treat STEMI), a neurovascular interventional procedure (NVI) (e.g., to treat an emergent large vessel occlusion (ELVO)), peripheral vascular intervention procedures (PVI) (e.g., for critical limb ischemia (CLI), etc.). Catheter-based medical procedures may include diagnostic catheterization procedures during which one or more catheters or other elongated medical devices (EMDs) are used to aid in the diagnosis of a patient's disease. For example, during one embodiment of a catheter-based diagnostic procedure, a contrast media is injected onto one or more arteries through a catheter and an image of the patient's vasculature is taken. Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one skilled in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedure.

Catheter-based procedure system 10 includes, among other elements, a bedside unit 20 and a control station 26. Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, a rail on the patient table 18, a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In an embodiment, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

Generally, the robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow the user or operator 11 to perform a catheter-based medical procedure via a robotic system by operating various controls such as the controls and inputs located at the control station 26. Bedside unit 20, and in particular robotic drive 24, may include any number and/or combination of components to provide bedside unit 20 with the functionality described herein. A user or operator 11 at control station 26 is referred to as the control station user or control station operator and referred to herein as user or operator. A user or operator at bedside unit 20 is referred to as bedside unit user or bedside unit operator. The robotic drive 24 includes a plurality of device modules 32a-d mounted to a rail or linear member 60 (shown in FIG. 3). The rail or linear member 60 guides and supports the device modules. Each of the device modules 32a-d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with control station 26, allowing signals generated by the user inputs of control station 26 to be transmitted wirelessly or via hardwire to bedside unit 20 to control various functions of bedside unit 20. As discussed below, control station 26 may include a control computing system 34 (shown in FIG. 2) or be coupled to the bedside unit 20 through a control computing system 34. Bedside unit 20 may also provide feedback signals (e.g., loads, speeds, operating conditions, warning signals, error codes, etc.) to control station 26, control computing system 34 (shown in FIG. 2), or both.

Communication between the control computing system 34 and various components of the catheter-based procedure system 10 may be provided via a communication link that may be a wireless connection, cable connections, or any other means capable of allowing communication to occur between components. Control station 26 or other similar control system may be located either at a local site (e.g., local control station 38 shown in FIG. 2) or at a remote site (e.g., remote control station and computer system 42 shown in FIG. 2).

Catheter procedure system 10 may be operated by a control station at the local site, a control station at a remote site, or both the local control station and the remote control station at the same time. At a local site, user or operator 11 and control station 26 are located in the same room or an adjacent room to the patient 12 and bedside unit 20. As used herein, a local site is the location of the bedside unit 20 and a patient 12 or subject (e.g., animal or cadaver) and the remote site is the location of a user or operator 11 and a control station 26 used to control the bedside unit 20 remotely. A control station 26 (and a control computing system) at a remote site and the bedside unit 20 and/or a control computing system at a local site may be in communication using communication systems and services 36 (shown in FIG. 2), for example, through the Internet. In an embodiment, the remote site and the local (patient) site are away from one another, for example, in different rooms in the same building, different buildings in the same city, different cities, or other different locations where the remote site does not have physical access to the bedside unit 20 and/or patient 12 at the local site.

Control station 26 generally includes one or more input systems 28 configured to receive user inputs to operate various components or systems of catheter-based procedure system 10. In the embodiment shown, control station 26 allows the user or operator 11 to control bedside unit 20 to perform a catheter-based medical procedure. For example, input systems 28 may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In one embodiment, input systems 28 may include one or more touch screens, joysticks, scroll wheels, and/or buttons. In addition to input systems 28, the control station 26 may use additional user controls 44 (shown in FIG. 2) such as foot switches and microphones for voice commands, etc. Input systems 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. When an emergency stop button is pushed, the power (e.g., electrical power) is shut off or removed to bedside unit 20. When in a speed control mode, a multiplier button acts to increase or decrease the speed at which the associated component is moved in response to a manipulation of input modules 28. When in a position control mode, a multiplier button changes the mapping between input distance and the output commanded distance.

Device selection buttons allow the user or operator 11 to select which of the percutaneous intervention devices loaded into the robotic drive 24 are controlled by input systems 28. Automated move buttons are used to enable algorithmic movements that the catheter-based procedure system 10 may perform on a percutaneous intervention device without direct command from the user or operator 11. In one embodiment, input systems 28 may include one or more controls or icons (not shown) displayed on a touch screen (that may or may not be part of a display 30), that, when activated, causes operation of a component of the catheter-based procedure system 10. Input systems 28 may also include a balloon or stent control that is configured to inflate or deflate a balloon and/or deploy a stent. Each of the input systems 28 may include one or more buttons, scroll wheels, joysticks, touch screen, etc. that may be used to control the particular component or components to which the control is dedicated. In addition, one or more touch screens may display one or more icons (not shown) related to various portions of input systems 28 or to various components of catheter-based procedure system 10.

Control station 26 may include a display 30. In other embodiments, the control station 26 may include two or more displays 30. Display 30 may be configured to display information or patient specific data to the user or operator 11 located at control station 26. For example, display 30 may be configured to display image data (e.g., X-ray images, MRI images, CT images, ultrasound images, etc.), hemodynamic data (e.g., blood pressure, heart rate, etc.), patient record information (e.g., medical history, age, weight, etc.), lesion or treatment assessment data (e.g., IVUS, OCT, FFR, etc.). In addition, display 30 may be configured to display procedure specific information (e.g., procedural checklist, recommendations, duration of procedure, catheter or guidewire position, volume of medicine or contrast agent delivered, etc.). Further, display 30 may be configured to display information to provide the functionalities associated with control computing system 34 (shown in FIG. 2). Display 30 may include touch screen capabilities to provide some of the user input capabilities of the system.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with control station 26. In one embodiment, imaging system 14 may include a C-arm (shown in FIG. 1) that allows imaging system 14 to partially or completely rotate around patient 12 in order to obtain images at different angular positions relative to patient 12 (e.g., sagittal views, caudal views, anterior-posterior views, etc.). In one embodiment imaging system 14 is a fluoroscopy system including a C-arm having an X-ray source 13 and a detector 15, also known as an image intensifier.

Imaging system 14 may be configured to take X-ray images of the appropriate area of patient 12 during a procedure. For example, imaging system 14 may be configured to take one or more X-ray images of the head to diagnose a neurovascular condition. Imaging system 14 may also be configured to take one or more X-ray images (e.g., real time images) during a catheter-based medical procedure to assist the user or operator 11 of control station 26 to properly position a guidewire, guide catheter, microcatheter, stent retriever, coil, stent, balloon, etc. during the procedure. The image or images may be displayed on display 30. For example, images may be displayed on display 30 to allow the user or operator 11 to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
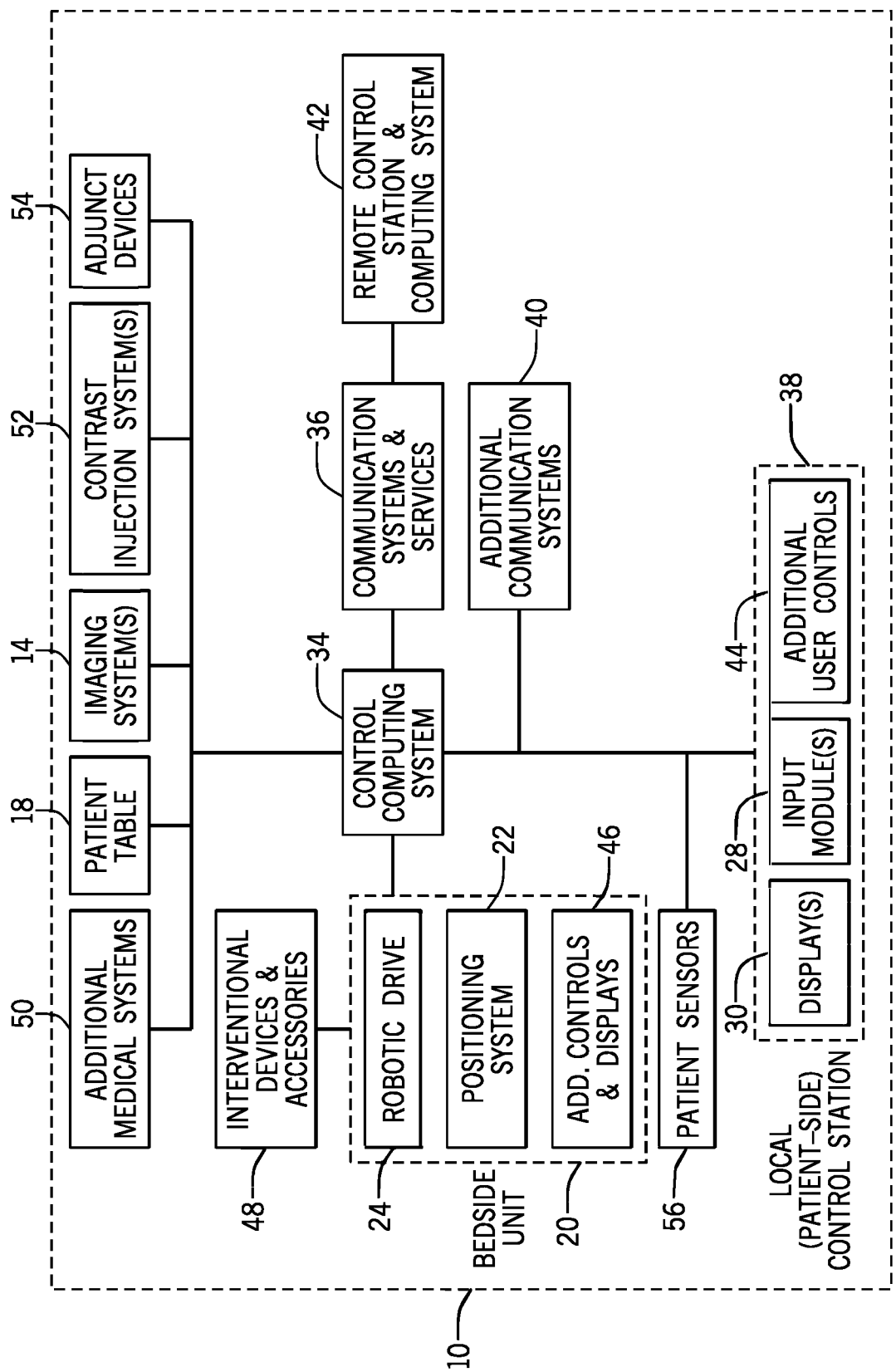
FIG. 2 is a schematic block diagram of an exemplary catheter-based procedure system in accordance with an embodiment.

FIG. 2 is a block diagram of catheter-based procedure system 10 in accordance with an exemplary embodiment. Catheter-procedure system 10 may include a control computing system 34. Control computing system 34 may physically be, for example, part of control station 26 (shown in FIG. 1). Control computing system 34 may generally be an electronic control unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, communications systems and services 36 (e.g., Internet, firewalls, cloud services, session managers, a hospital network, etc.), a local control station 38, additional communications systems 40 (e.g., a telepresence system), a remote control station and computing system 42, and patient sensors 56 (e.g., electrocardiogram (ECG) devices, electroencephalogram (EEG) devices, blood pressure monitors, temperature monitors, heart rate monitors, respiratory monitors, etc.). The control computing system is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In an embodiment, interventional devices and accessories 48 may include specialized devices (e.g., IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to generate control signals based on the user's interaction with input systems 28 (e.g., of a control station 26 (shown in FIG. 1) such as a local control station 38 or a remote control station 42) and/or based on information accessible to control computing system 34 such that a medical procedure may be performed using catheter-based procedure system 10. The local control station 38 includes one or more displays 30, one or more input systems 28, and additional user controls 44. The remote control station and computing system 42 may include similar components to the local control station 38. The remote 42 and local 38 control stations can be different and tailored based on their required functionalities. The additional user controls 44 may include, for example, one or more foot input controls. The foot input control may be configured to allow the user to select functions of the imaging system 14 such as turning on and off the X-ray and scrolling through different stored images. In another embodiment, a foot input device may be configured to allow the user to select which devices are mapped to scroll wheels included in input systems 28. Additional communication systems 40 (e.g., audio conference, video conference, telepresence, etc.) may be employed to help the operator interact with the patient, medical staff (e.g., angio-suite staff), and/or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

Figure 3:
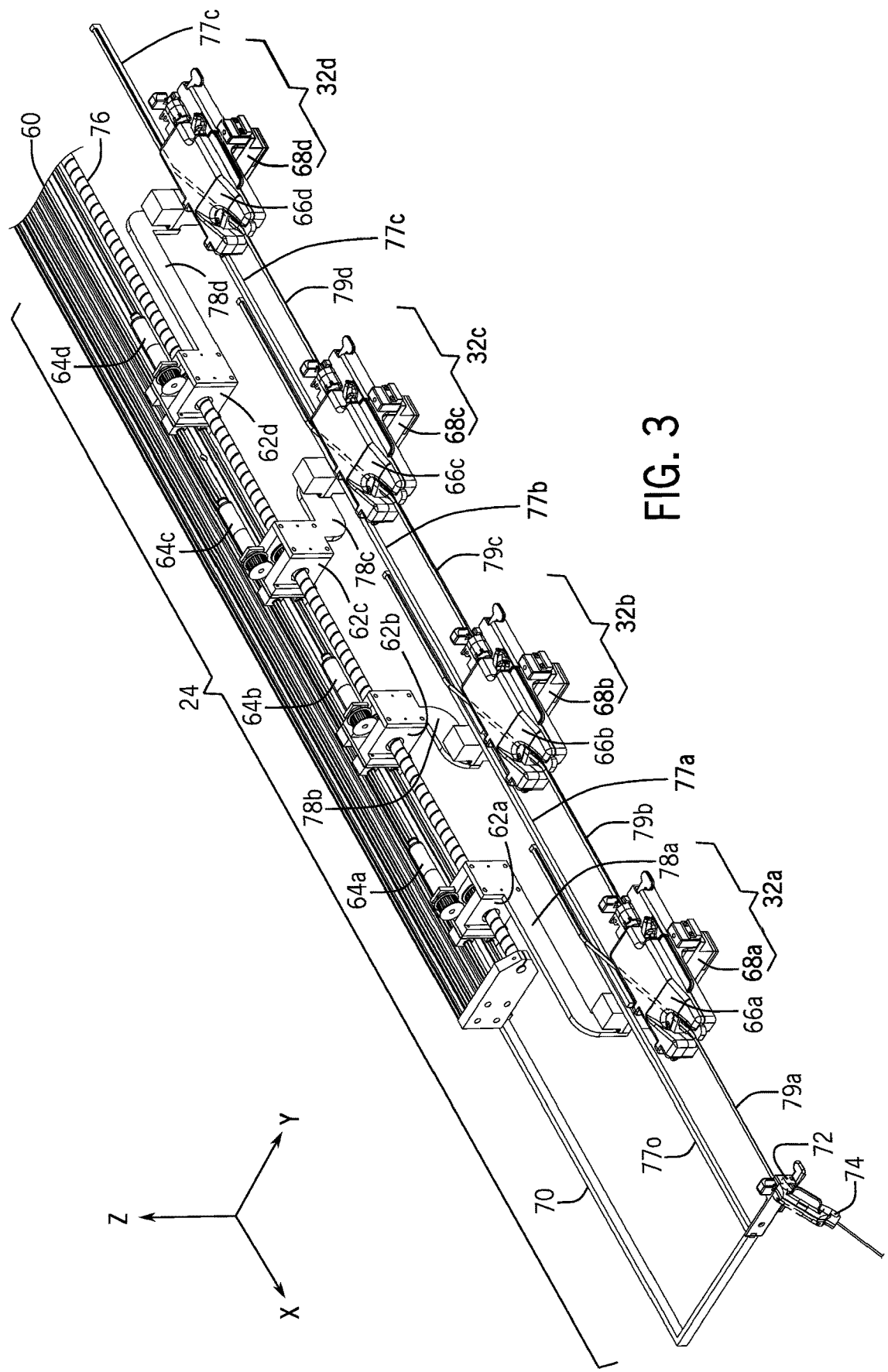
FIG. 3 is a perspective view of a robotic drive for a catheter-based procedure system in accordance with an embodiment.

As mentioned, control computing system 34 is in communication with bedside unit 20 which includes a robotic drive 24, a positioning system 22 and may include additional controls and displays 46, and may provide control signals to the bedside unit 20 to control the operation of the motors and drive mechanisms used to drive the percutaneous intervention devices (e.g., guidewire, catheter, etc.). The various drive mechanisms may be provided as part of a robotic drive 24. FIG. 3 is a perspective view of a robotic drive for a catheter-based procedure system 10 in accordance with an embodiment. In FIG. 3, a robotic drive 24 includes multiple device modules 32a-d coupled to a linear member 60. Each device module 32a-d is coupled to the linear member 60 via a stage 62a-d moveably mounted to the linear member 60. A device module 32a-d may be connected to a stage 62a-d using a connector such as an offset bracket 78a-d. In another embodiment, the device module 32a-d is directly mounted to the stage 62a-d. Each stage 62a-d may be independently actuated to move linearly along the linear member 60. Accordingly, each stage 62a-d (and the corresponding device module 32a-d coupled to the stage 62a-d) may independently move relative to each other and the linear member 60. A drive mechanism is used to actuate each stage 62a-d. In the embodiment shown in FIG. 3, the drive mechanism includes independent stage translation motors 64a-d coupled to each stage 62a-d and a stage drive mechanism 76, for example, a lead screw via a rotating nut, a rack via a pinion, a belt via a pinion or pulley, a chain via a sprocket, or the stage translation motors 64a-d may be linear motors themselves. In some embodiments, the stage drive mechanism 76 may be a combination of these mechanisms, for example, each stage 62a-d could employ a different type of stage drive mechanism. In an embodiment where the stage drive mechanism is a lead screw and rotating nut, the lead screw may be rotated and each stage 62a-d may engage and disengage from the lead screw to move, e.g., to advance or retract. In the embodiment shown in FIG. 3, the stages 62a-d and device modules 32a-d are in a serial drive configuration.

Each device module 32a-d includes a device module 68a-d and a cassette 66a-d mounted on and coupled to the device module 68a-d. In the embodiment shown in FIG. 3, each cassette 66a-d is mounted to the device module 68a-d in a vertical orientation. In other embodiments, each cassette 66a-d may be mounted to the device module 68a-d in other mounting orientations. Each cassette 66a-d is configured to interface with and support a proximal portion of an EMD (not shown). In addition, each cassette 66a-d may include elements to provide one or more degrees of freedom in addition to the linear motion provided by the actuation of the corresponding stage 62a-d to move linearly along the linear member 60. For example, the cassette 66a-d may include elements that may be used to rotate the EMD when the cassette is coupled to the device module 68a-d. Each device module 68a-d includes at least one coupler to provide a drive interface to the mechanisms in each cassette 66a-d to provide the additional degree of freedom. Each cassette 66a-d also includes a channel in which a device support 79a-d is positioned, and each device support 79a-d is used to prevent an EMD from buckling. A support arm 77a, 77b, and 77c is attached to each device module 32a, 32b, and 32c, respectively, to provide a fixed point for support of a proximal end of the device supports 79b, 79c, and 79d, respectively. The robotic drive 24 may also include a device support connection 72 connected to a device support 79, a distal support arm 70 and a support arm 77o. Support arm 77o is used to provide a fixed point for support of the proximal end of the distal-most support arm 79a housed in the distal most device module 32a. In addition, an introducer interface support (redirector) 74 may be connected to the device support connection 72 and an EMD (e.g., an introducer sheath). The configuration of robotic drive 24 has the benefit of reducing volume and weight of the drive robotic drive 24 by using actuators on a single linear member.

To prevent contaminating the patient with pathogens, healthcare staff use aseptic technique in a room housing the bedside unit 20 and the patient 12 or subject (shown in FIG. 1). A room housing the bedside unit 20 and patient 12 may be, for example, a cath lab or an angio suite. Aseptic technique consists of using sterile barriers, sterile equipment, proper patient preparation, environmental controls and contact guidelines. Accordingly, all EMDs and interventional accessories are sterilized and can only be in contact with either sterile barriers or sterile equipment. In an embodiment, a sterile drape (not shown) is placed over the non-sterile robotic drive 24. Each cassette 66a-d is sterilized and acts as a sterile interface between the draped robotic drive 24 and at least one EMD. Each cassette 66a-d can be designed to be sterile for single use or to be re-sterilized in whole or part so that the cassette 66a-d or its components can be used in multiple procedures.

As previously discussed, embodiments of a control station 26 can include a variety of different input systems for controlling the bedside unit 20. Input systems can include a variety of different input controls (for example, buttons, scroll wheels, joysticks, etc.) that can be manipulated by a user to control the robotic drive 24. These input controls can be arranged in different layouts or patterns on the input system so that a user can easily reach each of them without taking their hands off of the controls. This may be useful, for example, so that the user can simultaneously and independently control the movement of multiple different EMDs or device modules 32. Additionally, embodiments of an input system can be configured to operate in a variety of different control modes. In each control mode, different functions can be assigned to each of the input controls based on, amongst other factors, the procedure being performed, which device or devices are being controlled, user preferences, or any other factors. The input system can be configured to switch between different control modes to reassign functions to at least one of the input controls in response to the user or the control computing system 34.

In some embodiments, the body of an input system can be configured to be held in the hands of a user as the user manipulates controls coupled thereto. The term handheld refers to the capability of being held by at least one hand of a user while the user manipulates one or more controls coupled thereto with the at least one hand. The term handheld includes but is not limited to having dimension and weight to facilitate carrying by a user and manipulation of one or more controls coupled thereto while being carried, whether or not removably mountable to a fixed support. The term handheld includes but is not limited to having a structure of dimension and/or weight which does not facilitate carrying by a user.

Figure 4:
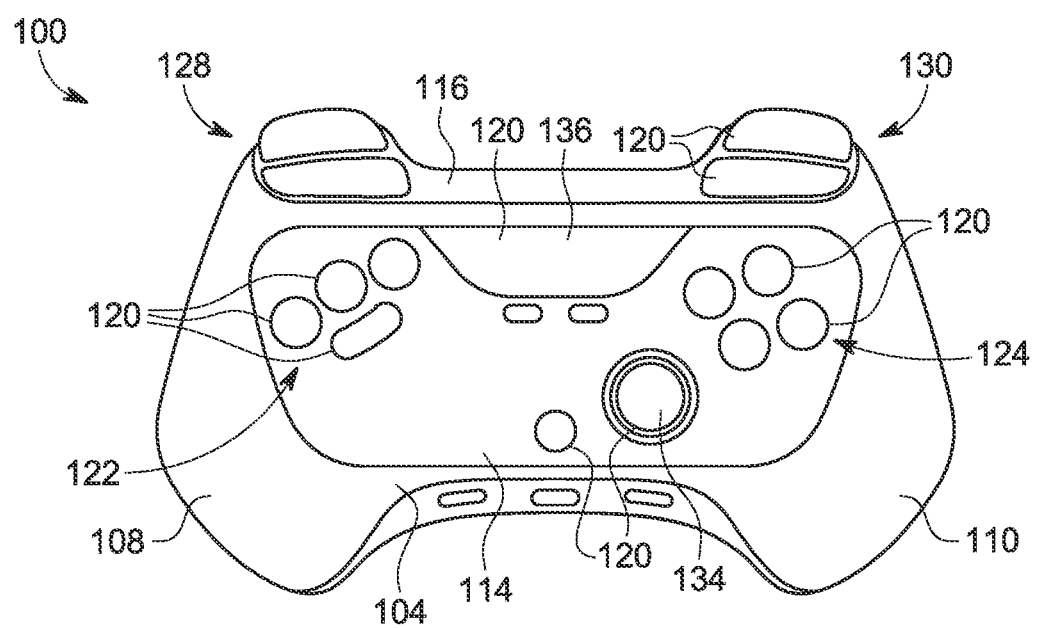
FIG. 4 is a perspective view of a handheld input system for a catheter-based procedure system in accordance with an embodiment.

An input system may be fixed to or integrated with a surface of the control station 26, or an input system may be configured to selectively operate in one of two or more of these arrangements. FIG. 4 illustrates a top-down view of a handheld input system 100 for controlling a catheter-based procedure system to perform a catheter-based medical procedure in accordance with an embodiment. The handheld input system 100 includes a body 104 with a left extension 108 and a right extension 110 extending from opposite lateral sides of the body 104. The left and right extensions 108, 110 are configured to be held by the user's left and right hands, respectively, and function as handles or handle portions to enable secure gripping of the handheld input system 100 by the user. A top surface 114 and a front surface 116 of the handheld input system 100 include various input controls 120 that are arranged so that they can be manipulated, actuated, or otherwise interacted with by at least one of the digits of the left and right hands of the user while the user holds the body 104.

The illustrated handheld input system 100 includes two groups of input controls 120—a left input array 122 and a right input array 124—arranged on the top surface 114 proximate the left and right sides of the body 104. When the handheld input system 100 is held by a user, the left and right input arrays 122, 124 are respectively positioned within the range of motion of the left and right thumbs of a user. Similarly, input controls 120 positioned on the front surface of the handheld input system 100 are grouped in a left shoulder group 128 and a right shoulder group 130 that are respectively within the range of motion the left and right index fingers of the user. Thus, the left input array 122 is configured so that it can be manipulated by a thumb of a left hand of the user, and the shoulder input group 128 is configured so that it can be manipulated by the index fingers and/or the middle fingers of the left hand of the user simultaneously with manipulation of input array 122 by the thumb of the left hand. Similarly, the right input array 124 is configured so that it can be manipulated by a thumb of a right hand of the user, and the shoulder input group 130 is configured so that it can be manipulated by the index fingers and/or the middle fingers of the right hand of the user simultaneously with manipulation of input array 124 by the thumb of the right hand.

It should be noted that the any input system described herein may be of dimension and weight to be carried by a user or integrated with the control station 26. An input system configured to be carried by a user may also be configured for removable mounting to the control station 26 or other fixed support.

In some embodiments, handheld input systems can include additional input controls that can be grouped with, or separate from, other input controls 120. For example, the top surface 114 of the illustrated handheld input system 100 further includes multiple input controls 120 that are positioned centrally with respect to the body 104, and a directional input control 134 positioned proximate the right input array 124 so that it can be manipulated by the right thumb of the user. The directional input controls 134 may be a knob, a joystick, a directional pad, a touch pad, or any other input control that can be manipulated by a user to command the robotic drive 24 to move an EMD and/or a device module 32 in multiple different directions. In other embodiments, however, another type of input control may be used. Additionally, the handheld input system 100 includes a touchpad input control 136 positioned between the left and right input arrays 122, 124 proximate the front side of the top surface 114.

Figure 5:
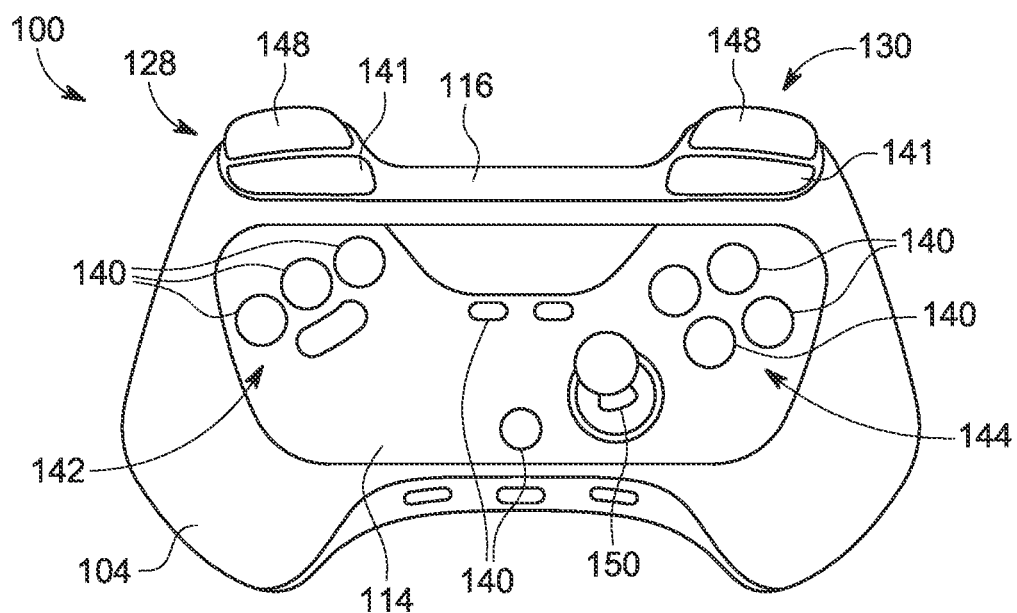
FIG. 5 is a perspective view of a handheld input system including a joystick in accordance with an embodiment.

A variety of different input control types and configurations may be used for each of the input controls on embodiments of handheld input system. Referring to FIG. 5, the handheld input system 100 can include at least one binary input control, such as binary buttons 140, which may be arranged in various locations on the top surface 114 and the front surface 116. The left and right input arrays, for example, are configured as left and right button arrays 142, 144 that each include multiple binary buttons 140. Additionally, the left and right shoulder groups 128, 130 each include a binary shoulder button 141 proximate a top side of the front surface 116, and three binary buttons 140 are positioned on the top surface 114 between the two button arrays 142, 144. When manipulated by the user, each of the binary buttons 140 can send a control signal indicating that that binary button 140 has been pressed. For example, at least one binary button 140 can be configured to send a control signal while the binary button 140 is held in a pressed state by the user, or whenever the binary button 140 is switched between the pressed and unpressed state.

Some handheld input systems can include at least one analog input control that sends a control signal which may vary between a minimum and a maximum value. In the illustrated embodiment, for example, the left shoulder group 128 and the right shoulder group 130 each include an analog trigger 148 arranged on the front surface 116 of the handheld input system 100 below the corresponding one of the shoulder buttons 141. The analog triggers 148 are configured to be pulled by at least one of the user's fingers through a range of positions between an unpulled (or unpressed) position and a fully-pulled (or fully-pressed) position, and each analog trigger 148 can include a biasing element (not shown) that biases the analog trigger 148 into the unpulled position once it is released by the user. Additionally, each analog trigger 148 is configured to send a control signal that varies based on the position of the analog trigger 148. For example, at least one analog trigger 148 can be configured to send a control signal that has a first value when the analog trigger is in the unpulled position, a second value when the analog trigger is in the pulled position, or a third value that can be interpolated between the first and second values based on when the analog trigger 148 is relative to the unpulled and fully-pulled positions.

Figure 6:
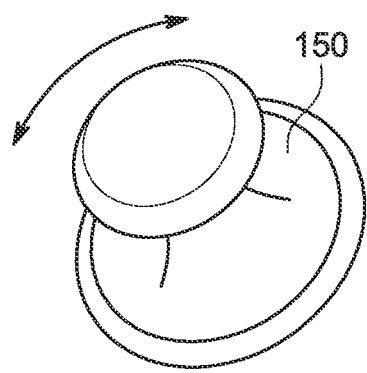
FIG. 6 is a detailed perspective view of a joystick in accordance with an embodiment.

In some embodiments, an analog input control can be configured as a tilting joystick 150 that can be manipulated by the user's right thumb. FIG. 6 illustrates a detailed view of the joystick 150 used with the handheld input system 100 of FIG. 5. In addition to providing a control signal that varies based on how far the joystick 150 is tilted away from its vertical resting position, the control signal may also vary based on the direction that the joystick 150 is tilted. For example, the joystick 150 may be configured to send a control signal that indicates how far and in what direction a user has moved the joystick 150. In some embodiments, a joystick (or other directional analog input) may be configured to send a control signal that only indicates the direction that it is tilted in or how far it has been tilted. A joystick may also be configured to only send a control signal when the joystick is tilted in one or more specific directions or ranges of directions. Additionally or alternatively, the control computing system 34 may be configured to only process or act based on certain aspects of a control signal, for example the direction or tilt angle of a joystick.

Some handheld input systems can include at least one input control configured as a scrolling or rotating input control. For example, the handheld input system 100 of FIG. 7 includes a scroll wheel 154 positioned on the top surface 114 and configured to be manipulated by the right thumb of the user. Such manipulation by the right thumb may occur simultaneously with manipulation of right shoulder button 141 and/or right analog trigger 148 with one or more fingers of the user's right hand. Manipulation by the right thumb and one or more fingers of the user's right hand may further occur simultaneously with manipulation of left shoulder button 141 and/or left analog trigger 148 with one or more fingers of the user's left hand.

Figure 7:
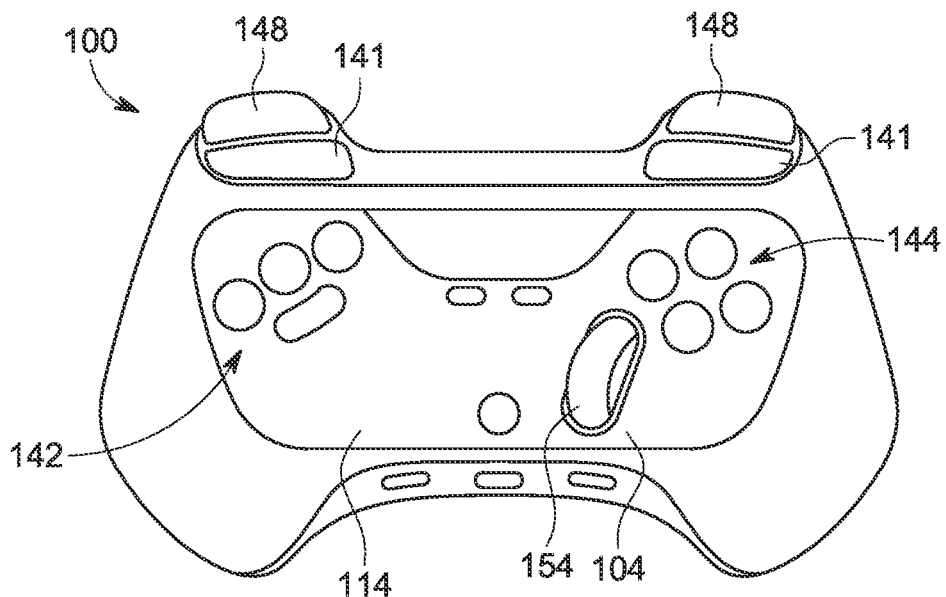
FIG. 7 is a perspective view of a handheld input system including an input control configured as a scroll wheel in accordance with an embodiment.
Figure 8:
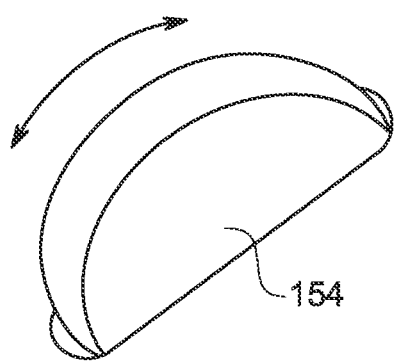
FIG. 8 is a detailed perspective view of the scroll wheel of FIG. 7.

FIG. 8 provides a detailed view of the scroll wheel 154 of FIG. 7. The scroll wheel 154 is partially enclosed within the handheld input system 100 so that a portion of the scroll wheel 154 projects outward from the top surface 114 and is accessible to the user, while a different portion of the scroll wheel is positioned within the body 104. The axis of rotation of the scroll wheel 154 is generally parallel to the top surface 114 so that, when it is rotated by a user, part of the exposed section of the scroll wheel 154 moves into the body 104 while part of the hidden section of the scroll wheel 154 moves out of the body 104 into view of the user. As the user rotates the scroll wheel 154 (or another scrolling input control), it provides a control signal which relays how far and in which direction the scroll wheel 154 is rotated to the control computing system 34.

In some embodiments, a scroll wheel 154 can include a plurality of detents configured to provide discrete rotational positions for the scroll wheel 154. As the scroll wheel 154 is rotated between these positions, the detents may provide the user with tactile feedback. For example, the detents may provide initial resistance against rotation of the scroll wheel 154, but can then push the scroll wheel 154 once it is rotated far enough, thereby causing it to jump or "pop" into the next rotational position. The scroll wheel 154 can be configured to send a control signal each time it is moved between the rotational positions defined by the detents, providing a first control signal when the scroll wheel 154 is rotated in a first direction or a second control signal when it is rotated in a second direction opposite the first.

Figure 9:
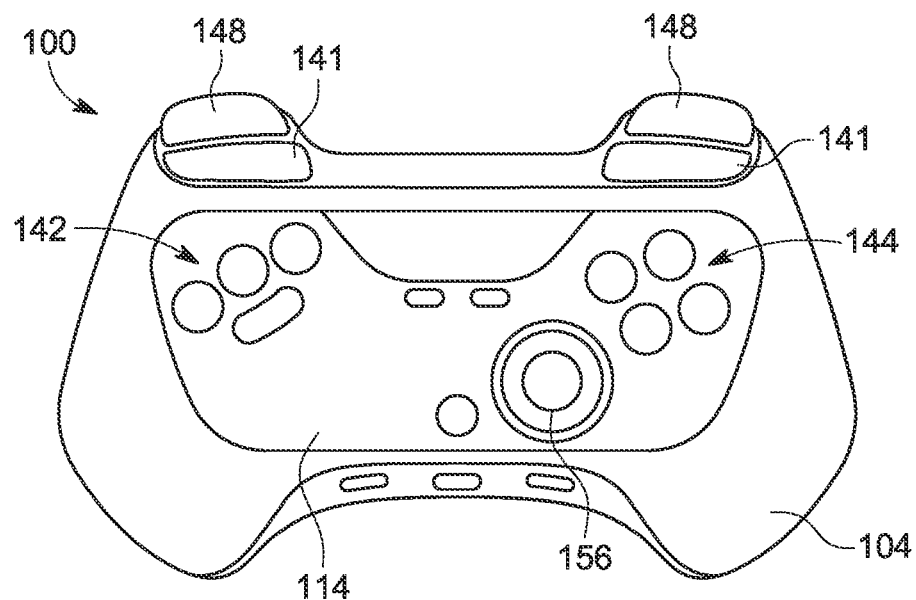
FIG. 9 is a perspective view of a handheld input system including an input control configured as a jog wheel in accordance with an embodiment.
Figure 10:
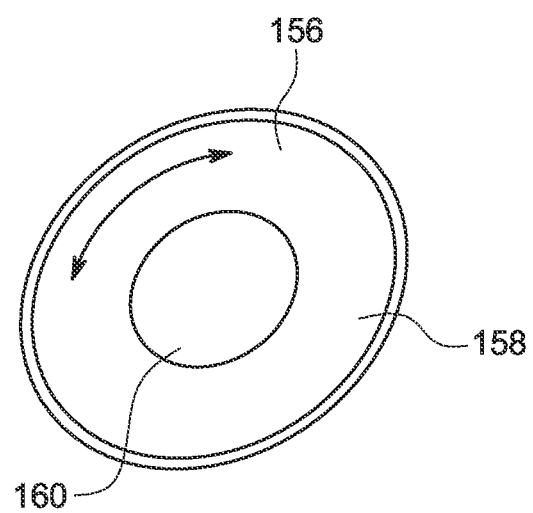
FIG. 10 is a detailed perspective view of the jog wheel of FIG. 9.
Figure 11:
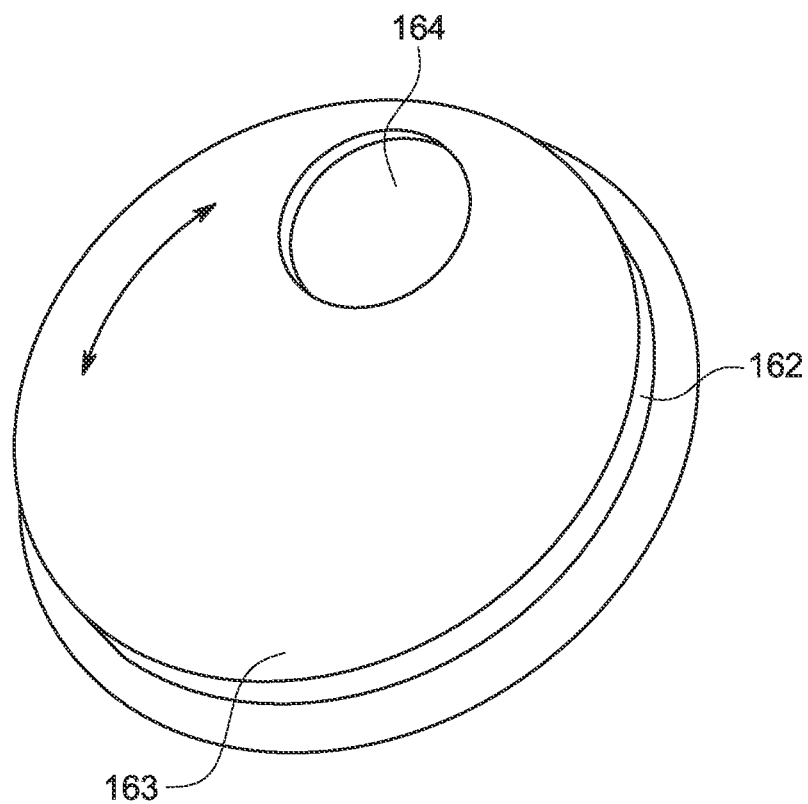
FIG. 11 is a perspective view of an input control configured as a dial in accordance with an embodiment.
Figure 12:
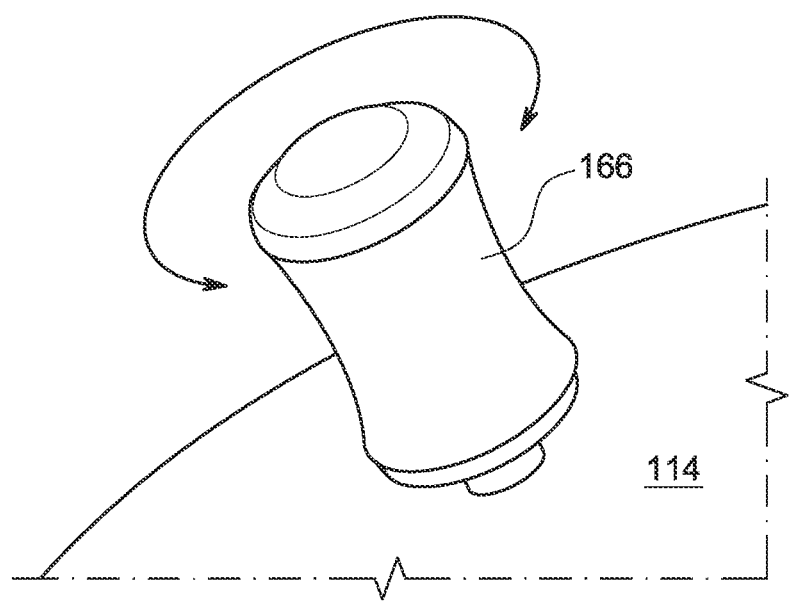
FIG. 12 is a perspective view of an input control configured as a knob in accordance with an embodiment.

Some embodiments of a handheld input system can include a scrolling input control in a different configuration. For example, FIG. 9 illustrates the handheld input system 100 with a scrolling input control configured as a jog wheel 156, which is illustrated in detail in FIG. 10. The jog wheel 156 is generally flat and has an axis of rotation that perpendicular to the top surface 114 so that, when rotated by the user, the jog wheel 156 spins without moving into or out of the body 104. The illustrated jog wheel 156 includes a disk portion 158 that rotates around a hub 160. In some embodiments, the hub 160 can be configured as an input control that may be pressed by the user. FIG. 11 illustrates another scrolling input control configured as a dial 162. As with the jog wheel 156 of FIGS. 9 and 10, the dial 162 has an axis of rotation that is perpendicular to the top surface 114 of the handheld input system 100. The dial 162 may project away from the top surface to a raised face 163, which can include a recess 164 configured to be engaged by a user's finger to rotate the dial 162. As illustrated in FIG. 12, a scrolling input control can additionally be configured as a knob 166 that can be manipulated by at least one digit of a user's hand.

Figure 13:
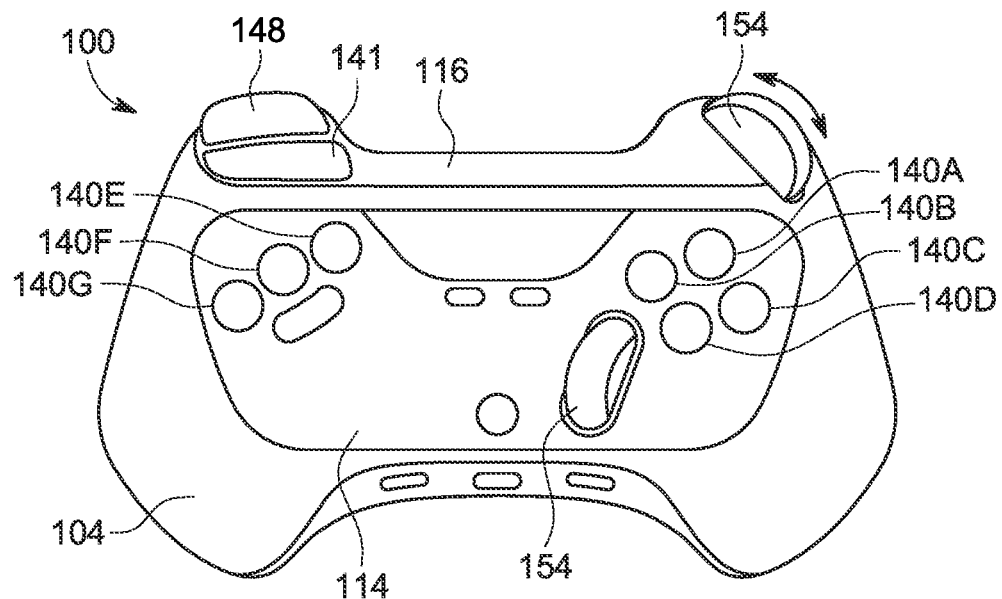
FIG. 13 is a perspective view of a handheld input system including two scroll wheels in accordance with an embodiment.

Further still, a handheld input system can include more than one scrolling input control. FIG. 13 illustrates a handheld input system 100 that includes two scroll wheels 154. The first scroll wheel 154 is arranged on the top surface 114 and is configured to be manipulated by a right thumb of a user, and the second scroll wheel 154 is positioned on the front surface 116 and is configured to be manipulated simultaneously, if desired, by a different finger, on the user's right hand, such as the index finger of the middle finger. This may be useful, for example, in order to control two degrees of freedom of an EMD with scrolling input controls (as described in reference to FIGS. 16 and 17), and/or one degree of freedom of each of two different EMDs.

Figure 14:
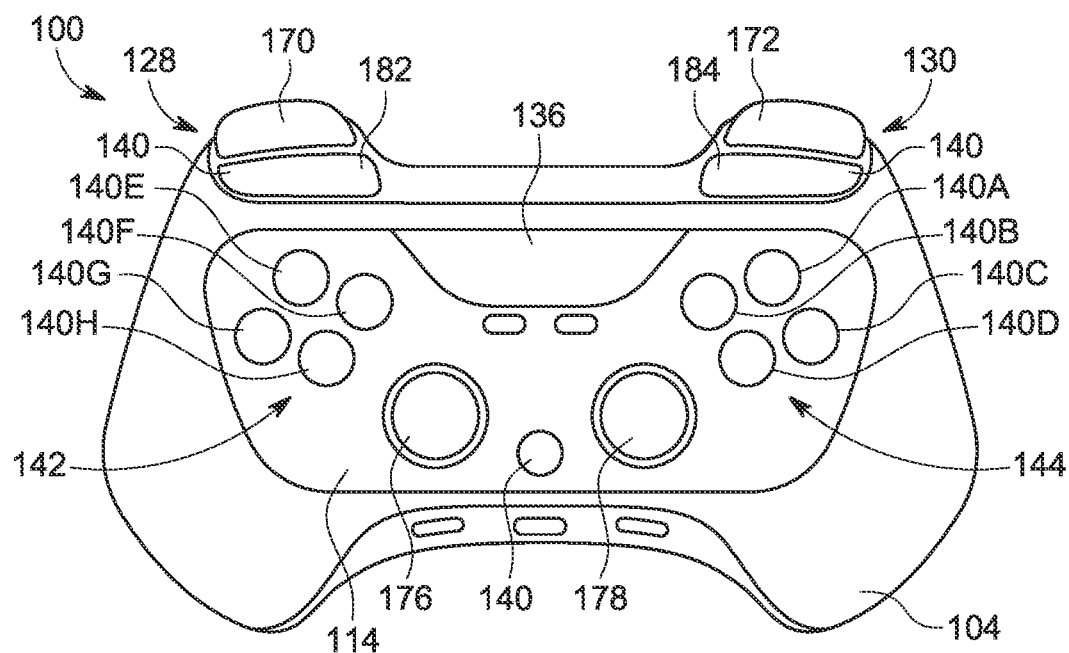
FIG. 14 is a perspective view of a handheld input system including binary input controls, analog input controls, scrolling input controls, and touch input controls in accordance with an embodiment.

FIG. 14 illustrates a handheld input system 100 that includes two jog wheels 176, 178 that may be manipulated by a user's left and right thumbs, respectively and simultaneously, if desired. The FIG. 14 arrangement may be useful, for example, in order to control two degrees of freedom of an EMD, and/or one degree of freedom of each of two different EMDs.

Some embodiments of a handheld input system can include a touch input control (such as the touchpad 136), which may be configured as at least one of a binary input control, an analog input control, and a scrolling input control. For example, a capacitive touch pad can be configured as a directional swipe pad that may be used as an alternative to a physical joystick. Embodiments of a jog wheel can be configured as a mechanical component that can be physically rotated by the user, or as a touch input control, such as a capacitive touch pad, can be used to simulate a mechanical jog wheel. Similarly, a touch input control can be used to simulate a scroll wheel.

Embodiments of a handheld input system can be configured to control a catheter-based procedure system in a variety of different modes that use various combinations of input controls as motion controls or selection controls. When used as a motion control, an input control can be configured to control axial and/or rotational movement of at least one EMD. Further, input controls that are used as motion controls may be configured to control movement of an EMD in a position control mode or a speed control mode.

Any of the above-described input controls, when used in a position control mode, can instruct the robotic drive 24 to actuate an EMD by a prescribed increment when the input control is activated. When controlling axial movement in a position control mode, an input control can command at least one device module 32 to move a discrete distance in the distal or proximal direction. When controlling the rotational movement of an EMD in a position control mode, an input control can command a device module 32 to rotate the EMD a discrete angle in the clockwise or counterclockwise direction. When a position motion command is issued in a closed-loop system, the control computing system 34 can compare the commanded increment or position with a measured increment or position. If the commanded value is different than the measured value, the control computing system 34 can close the loop by providing an additional motion command to correct the difference.

When used in a speed control mode, any of the above-described input controls can instruct the robotic drive 24 to continuously actuate an EMD at a prescribed rate while the input control is activated by the user. When controlling axial movement, an input control in speed control mode can command at least one device module 32 to move in the distal or proximal direction continuously at the prescribed rate until the user deactivates the input control (or a limit of the robotic drive 24 is reached). Similarly, an input control in speed control mode can command at least one device module 32 to continuously rotate at the prescribed rate as long as the input control is activated. When a speed motion command is issued in a closed-loop system, the control computing system 34 compares the commanded speed with the measured speed and, if a difference is detected, adjust the movement speed to close the loop.

With continued reference to FIG. 14, embodiments of the handheld input system 100 can configured to control the robotic drive 24 of a catheter-based procedure system using multiple control modes. The handheld input system 100 includes two analog input controls configured as a left analog trigger 170 and a right analog trigger 172, and two scrolling input controls configured as a left jog wheel 176 and a right jog wheel 178. Additionally, the handheld input system 100 includes multiple binary buttons 140 that are grouped into a left or right button array 142, 144, configured as a left shoulder button 182 or a right shoulder button 184, or arranged proximate the center of the top surface 114. Each of the binary buttons 140, analog triggers 170, 172, and jog wheels 176, 178 can be configured to operate in a speed control mode and a position control mode.

When used in a position control mode, the binary buttons 140 may be configured to instruct the robotic drive 24 to actuate a selected EMD or device module 32 by the prescribed increment each time the user activates binary button 140. For example, the left shoulder button 182 can be configured to command the robotic drive 24 to actuate (axially or rotationally) an EMD in a first direction by a prescribed increment and the right shoulder button 184 can be configured to actuate the EMD in a second, opposite direction by the same prescribed increment. In speed control mode, the binary buttons 140 device can be configured to instruct the robotic drive 24 to begin actuating an EMD to move axially or rotate at a prescribed rate pressed by the user, and can continue to do so until the user releases the binary button 140 or a limit of the robotic drive 24 is reached. Similar to how they function in a position control mode, left and right shoulder buttons 182, 184 can be configured to command a robotic drive 24 to actuate (axially or rotationally) an EMD in a first direction and or a second direction opposite the first.

The left and right analog triggers 170, 172 can be configured to instruct the robotic drive 24 to move or rotate a selected EMD or device module 32 by a variable increment when used in a position control mode, or at a variable rate when a speed control mode. When one of the analog triggers 170, 172 is fully pulled by the user, it may command the robotic drive 24 to actuate (axially or rotationally) a selected EMD by the full value of a prescribed increment. If one of the analog triggers 170, 172 is partially pulled by the user, however, it may command the robotic drive 24 to actuate the EMD by a fraction of the prescribed increment corresponding to how far the trigger was pulled. When in a speed control mode, the analog triggers 170, 172 may similarly be configured to instruct the robotic drive 24 to actuate (axially or rotationally) an EMD at a fraction of a full prescribed rate when the analog trigger 170, 172 is partially pulled by a user. In some embodiments, the left analog trigger 170 can be configured to command the robotic drive 24 to move or rotate an EMD in a first direction, while the right analog trigger 172 can be configured to command the robotic drive 24 to move or rotate an EMD in a second direction opposite the first. Thus, when used together, the left and right analog triggers 170, 172 can provide speed controls and/or position controls for moving or rotating an EMD. Additionally or alternatively, the left and right analog triggers 170, 172 can be configured to command the robotic drive 24 to move or rotate an EMD in the same direction, but at different rates.

As with binary and analog input controls, scrolling input controls can be configured in a position or speed control mode. When configured in a position control mode, the left and right jog wheels 176, 178 can be configured to instruct the robotic drive 24 to move or rotate an EMD by a discrete increment each time the user rotates the jog wheels 176, 178 a nominal angular distance. For a jog wheel 176, 178 that includes detents, this nominal angular distance may correspond to the angular distance between the discrete rotational positions created by the detents. Thus, the robotic drive 24 to move or rotate an EMD by the prescribed increment each time the user rotates the left and right a jog wheels 176, 178 between rotational positions. If a jog wheel 176, 178 is moved between multiple rotational positions, the total commanded rotational or angular motion may be determined by multiplying the prescribed increment by the number of times the user moved the jog wheel 176, 178 between different rotational positions. The direction of the commanded EMD motion may depend on the direction that the left or right jog wheel 176, 178 is rotated. Rotating a jog wheel 176, 178 in a clockwise direction may instruct the robotic drive 24 to move or rotate the EMD in a first direction, and rotating the jog wheel 176, 178 in a counterclockwise direction may instruct the robotic drive 24 to move or rotate the EMD in a second direction opposite the first direction.

When configured in a speed control mode, a scrolling input control may function similarly to a throttle, where rotation of the scrolling device in one direction increases a commanded rate of EMD motion, and rotation in the opposite direction decreases the commanded rate of EMD motion. In the illustrated embodiment, the left and right jog wheel 176, 178 can have a neutral position in which they do not provide an instruction for the robotic drive 24 to move or rotate and EMD. Each time one of the jog wheels 176, 178 is rotated a nominal angular distance it can instruct the robotic drive 24 to either increase or decrease a rate of axial or rotational movement based on the direction that the user rotates the jog wheel 176, 178. The robotic drive 24 can continue to move or rotate the EMD at the commanded rate until the user adjusts the rate by moving the jog wheel 176, 178 to a different rotational position. To stop the robotic drive 24 from moving or rotating the EMD, the user can return the corresponding jog wheel 176, 178 to the neutral position.

Although the use of binary input controls, analog input controls, and scrolling input controls in position and speed control modes has been described in reference to the binary buttons 140, analog triggers 170, 172, and jog wheels 176, 178 in FIG. 14, it should be appreciated that some embodiments of a handheld input system can include at least one input control that is different than those of the illustrated embodiments. Additionally or alternatively, a handheld control module can include input controls that are configured in a different arrangement than those of the illustrated embodiments.

In some operating modes, the relationship between the binary, analog, and scrolling input controls and the increment of commanded axial movement or rotation of an EMD may be fixed. When operating in such a mode, the value of the prescribed increments and the prescribed rates for position controls and speed controls, respectively, may be fixed for an input control. In other modes of operation, however, the relationship between the binary, analog, and scrolling input controls and the amount of commanded axial movement or rotation of an EMD may be configurable by the user or by the control computing system 34. For example, the handheld input system 100 of FIG. 14 can include at least one binary button 140 configured as a scaling input that can adjust (for example, increase or decrease) the prescribed increment or the prescribed rate associated with at least one input control. A handheld input system 100 with one binary button 140 configured as a scaling input can be configured to cycle between multiple preset options for the prescribed increments and rates for at least one input control.

A handheld input system 100 can include multiple binary buttons 140 that are configured as scaling inputs for adjusting the prescribed increment and rate for one input control or group of input controls. The left button array 142 or the right button array 144 can include two binary buttons 140 configured as scaling inputs—one binary button 140 being configured to increase the prescribed increment and rate associated with the associated input control (s), the other binary button 140 being configured to decrease the prescribed increment and rate. For example, when configured to adjust movement instructions issued by the jog wheels 176, 178 (or any other scrolling input control) in a position control mode, a binary button 140 scaling input may adjust the amount of movement that is commanded each time the jog wheels 176, 178 are moved between the rotational positions created by the detents.

The scaling inputs can be configured so that, each time one is activated by the user, the prescribed rate and prescribed increments of the associated input control (s) may be increased or decrease by a predetermined value. Additionally or alternatively, the prescribed increment or rate of an input control may be increased or decreased based on a scaling factor each time a corresponding scaling inputs is pressed. For example, a handheld input system 100 can be configured so that the prescribe rate associated with an analog triggers 170, 172 in a speed control mode is multiplied by a scaling factor (greater than one to increase the prescribed rate or less than one to decrease the prescribed rate) when one of the scaling inputs is pressed. In some embodiments, a handheld input system 100 can include at least binary button 140 that is associated with a specific scaling factor. While that binary button 140 is held by the user, motion commands issued using the handheld input system 100 may be multiplied by the associated scaling factor.

In some embodiments, a handheld input system can be configured with selection verification features that require a user to confirm that the desired EMD and/or device module 32 has been selected before any motion commands are sent to the robotic drive 24. In the illustrated embodiment, at least one of the binary buttons 140 on the handheld input system 100 can be configured as a selection control that can be used to select which of the device modules 32 and/or which of the EMDs will be controlled by the motion controls. For example, the left button array 142 or the right button array 144 can be configured as a selection array in which each of the binary buttons 140 corresponds to a single EMD or device module 32, or to a group of multiple EMDs and/or device modules 32. Each of the selection controls in a selection array may be arranged in a logical order coordinating with the EMD's orientation in use, which may mimic their orientation in manual intervention. For example, the selection controls may be arranged based on their size, where the device with the largest diameter (for example, a guide catheter) corresponds to the leftmost selection control, the device with the smallest diameter (for example, a guide wire) corresponds to the rightmost selection control, and any selection controls corresponding to other EMDs are positioned in between.

While some handheld input systems 100 can be configured to control an EMD or device module 32 after the corresponding selection control is momentarily pressed, other embodiments made be configured in a continuous activation mode that requires a user to hold a selection control in order for motion commands to be sent to the corresponding device module 32. If the user tries to use a motion control to move an EMD or device module 32 without holding the selection control, the robotic drive 24 would not move any devices. Additionally, the robotic drive 24 may stop moving a device if the user releases the corresponding selection control while the device is moving because a corresponding instruction would no longer be sent to the robotic drive 24. This may be useful, for example, in order to help prevent incidental movement of an EMD or device module 32. A single selection control may be associated with one or more input controls such that it controls all instructions sent as a result of manipulation of the one or more input controls.

In order to select multiple EMDs or device modules 32 simultaneously, a user can hold multiple selection controls simultaneously. Some selection controls can be configured to be assigned to specific device combinations of EMDs and/or device modules 32. Additionally or alternatively, a handheld input system 100 could include a binary button 140 configured as a grouping button that, when held, causes the control computing system 34 or the handheld input system 100 to store or record any selection controls that are pressed while the grouping button is held even after those selection controls are released. While the user continues to hold the grouping button, the handheld input system 100 can provide instructions to move or rotate any of the devices that are associated with the stored selection controls. When the grouping button is released by the user, the stored selection controls may be cleared.

In some embodiments, a directional input control, such as a joystick or directional pad, can be configured as a selection input control. For example, the positions around the joystick (e.g., up, down, left, and right) may correspond to different EMDs, device modules 32, or groups of devices. To select a device or group of devices, the user can manipulate the joystick to point to the desired device(s). Pointing the joystick between two positions would select the EMDs and/or device modules 32 corresponding to both positions. In another embodiment, an EMD or device module 32 can be selected by invoking an on-screen selection menu, and choosing one or more of the presented options. The input controls used for navigating the menu may be also be used as motion controls, while some embodiments can include separate input controls that are only used for menu navigation.

Using the button arrays 142, 144 and shoulder buttons 182, 184, the analog triggers 170, 172 and the jog wheels 176, 178 as motion controls, scaling inputs, and selection controls in various combinations of the above configurations, the handheld input system 100 of FIG. 14 can operate in various different control modes. In some embodiments, the handheld input system 100 may switch between control modes in response to information from the computing control computing system 34. For example, the handheld input system 100 can be configured to operate in different control modes during different parts of a procedure. Additionally or alternatively, the handheld input system 100 can switch control modes based on which EMDs or device modules 32 are selected, or in response to a user manually switching control modes.

In some control modes, a user can control axial movement of a selected EMD by manipulating the analog triggers 170, 172 and/or the shoulder buttons 182, 184 with their index fingers or middle fingers. In this control mode, the left button array 142 may be configured as a selection array, and the user may select an EMD or device module 32 to control. The handheld input system may be configured so that the right analog trigger 172 and the right shoulder button 184 (the right shoulder group 130) can instruct the robotic drive 24 to move the EMD in the distal direction, and the left analog trigger 170 and the left shoulder button 182 (the left shoulder group 128) can instruct the robotic drive 24 to move the EMD in the proximal direction. The left and right analog triggers 170, 172 can be configured in a speed control mode, and can therefore command variable speed axial motion based on how far the analog triggers 170, 172 are pulled by a user. Additionally, two binary buttons 140 in the right button array 144 may be configured as scaling inputs for adjusting the rate of axial motion commanded by the analog triggers 170, 172. One of the scaling inputs can be configured to increase the axial rate of motion (for example, by doubling the speed), while the other scaling input can be configured to reduce the axial rate of motion (for example, by halving the speed). An increased speed may be where the vasculature is not tortuous and has side branches that are easily avoided, and an even higher speed may be used for moving EMDs within other EMDs.

In some embodiments, and, for example, in place of right analog trigger 172, an analog rocker could be sprung to the center of its range, where manipulation in one direction commands axial motion in the distal direction, while manipulation of the rocker in the opposite direction commands axial motion in the proximal direction. Additionally, a binary button, for example a shoulder button, may be configured to reverse the direction of motion commanded by an analog trigger.

In addition to speed controls, the left shoulder button 182 and the right shoulder button 184 can be configured as position controls for moving the selected EMD in the proximal and axial directions, respectively. Additionally or alternatively, two binary buttons 140 in the right button array 144 may be configured as position controls for commanding axial movement of and EMD. In some control modes, the speed control and the position controls may be simultaneously available to the user, and in some control modes only one type of control will be available at a given time. Rotation of the EMD may be linked to at least one of the left and right jog wheels 176, 178, which may be manipulated by the corresponding thumbs of the user in order to instruct the robotic drive 24 to rotate the EMD. The jog wheels 176, 178 can be configured in a position control mode, and in some embodiments, the scaling inputs may be pressed by the user to adjust the relationship between rotation of the jog wheels 176, 178 and the rotation of the EMD.

In some control modes, a user may be able to simultaneously and independently control axial motion and rotational motion of two different EMDs using the thumbs and fingers of both hands as described above. For example, the handheld input system 100 can be configured so that the input controls on the left half of the handheld input system 100 control movement of one EMD, while input controls on the right half of the handheld input system 100 control movement of a second EMD. In some control modes, the left button array 142 and the right button arrays 144 may be configured as selection arrays for selecting which EMD or device module 32 will be controlled by the left and right sides of the handheld input system, respectively. In another control mode, the input controls on one side of the handheld input system 100 can be permanently assigned to an EMD or device module 32.

Input controls on the left and right shoulder groups 128, 130 can be configured to independently control axial movement of two different EMDs. For example, the analog triggers 170, 172 can be configured to instruct the robotic drive 24 to move the respective EMDs in a distal direction, while the shoulder buttons 182, 184 can instruct the robotic drive 24 to move the respective EMDs in a proximal direction. Rotation of the selected EMDs may be independently controlled using the left and right jog wheel 176, 178. In some embodiments, a handheld input system may only include one jog wheel, which may be configured to control rotation of both of the selected EMDs, or it can be configured to only control rotation of one of the EMDs According to some embodiments, the robotic system is configured so that the input controls instructing motion of the wire-based EMD are mapped to the device module holding the wire-based EMD. The identity of the device module holding the wire-based EMD may be detected with sensors in response to loading the EMD into the device module. Detection may employ contact or non-contact sensors, such as mechanical, electrical or visual sensors, or by a user input prompted by the system.

The controls on the right side of the input system 100 instruct motion of the device module which is holding the wire-based EMD. For example, jog wheel 178 can be rotated by the user's right thumb to rotate the wire-based EMD. Trigger 172 advances the wire-based EMD at a speed which corresponds with the degree to which the trigger is pulled by the user's right index finger. Shoulder button 184 can be pressed by the user's index finger to retract the wire-based EMD. Jog wheel 178 and either of trigger 172 and button 184 may be manipulated simultaneously.

The controls coupled to the left side of the input system 100 control a selected catheter. Button array 142 includes buttons 140E, 140F and 140G, and pressing one of the buttons (typically with the left thumb) selects a device module 1, 2 or 3 respectively such that manipulation of the controls on the left side of the input system 100 results in the sending of instructions to the selected device module. The input system 100 may allow multiple catheters to be selected by pressing the selection buttons 140E, 140F and 140G in series. Pressing button 140H may deselect any selected device modules. The left side of the input system 100 further includes controls 176, 170 and 182 to instruct the selected device module(s) to control the motion of the selected catheter, in the same way as the corresponding controls described above on the right side (e.g., using a left index finger and left thumb, simultaneously or otherwise).

In another embodiment, the controls for the wire-containing device module are not separated from controls of the catheter-containing device modules. For example, scroll wheel 154 is positioned on the upper right shoulder of input system 100 of FIG. 13 to be manipulated by the index finger of the right hand for linear motion. Four selection buttons 140A, 140B, 140C, 140D are arranged for device module selection by the right thumb, with each button corresponding to one of catheter 1, 2, 3 and the wire-based EMD. In one embodiment, tapping and releasing a button 140A, 140B, 140C or 140D selects the associated device module. In another embodiment, the user is required to hold depressed the button or buttons associated with the selected device modules to maintain selection thereof.

Scroll wheel 154 on top surface 114 of FIG. 13 may be be manipulated by the left thumb in order to control rotation of the device selected by the right thumb. The user can move their left hand off the scroll wheel 154 and select a device module with buttons 140E, 140F, and/or 140G, respectively assigned to Catheter 1, Catheter 2 and Catheter 3. When selecting a device module with the left thumb, the left index finger can manipulate buttons 141 and 148 to control linear motion of the left hand-mapped device, while the right thumb simultaneously selects another device or devices using buttons 140A, 140B, 140C, 140D and the right finger manipulates scroll wheel 154 to control linear motion of that device.

Figure 13B:
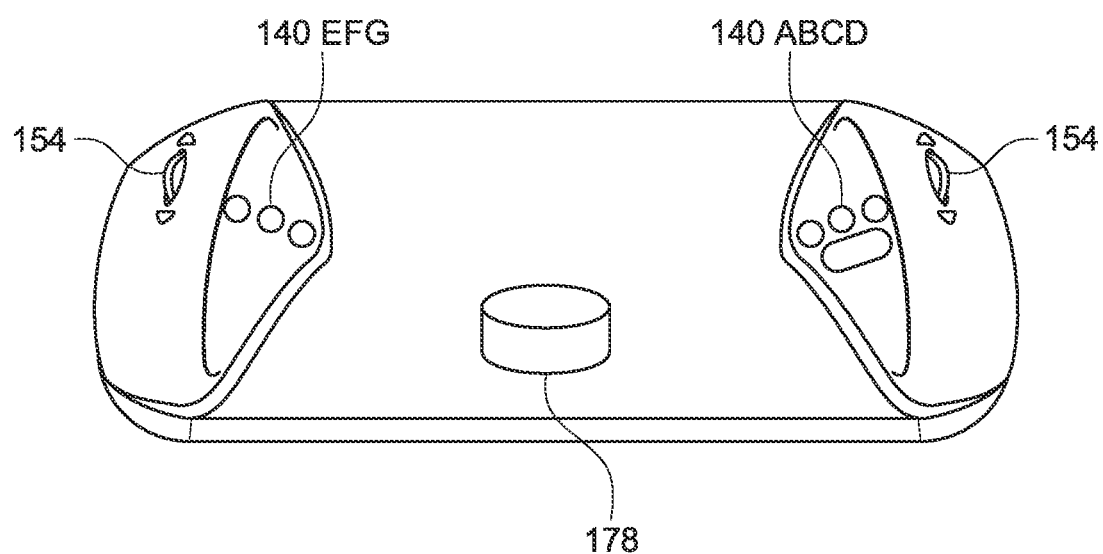
FIG. 13B is a perspective view of a handheld input system including two scroll wheels, a knob and selection buttons in accordance with an embodiment.

The same functionality and control scheme as described above for FIG. 13 can be applied to similarly-arranged controls in different housings. In another example, FIG. 13B shows the same functional controls as in FIG. 13, coupled to a handheld body designed to sit on or be integrated with a table/desk/console-type support. In one embodiment of operation, the linear motion control for the right hand-selected device(s) (i.e., selected by tapping and releasing one or more of buttons 140A, 140B, 140C and/or 140D, or by continuously depressing and holding the button(s) associated with the selected device modules) is right side scroll wheel 154 and the rotation control for the right hand-selected device is now a knob 178 located near the center of the support and manipulable by a finger or fingers on the left hand. To perform tasks described above which require two-independently controlled linear degrees of freedom of two EMDs, the user moves their hand from the knob 178 to the controls on the left, selects a device module using the left thumb and buttons 140E, 140F or 140G (either by tapping or by holding down associated button(s) 140E, 140F and/or 140G), and manipulates the left side scroll wheel 154 to instruct linear motion of a second EMD, while the right hand continues to operate as described above.

The following table describes operational modes of the FIG. 14 input system and the functions of various input controls in each operational mode according to some embodiments. Any module selection described in the table may require continuous activation of the corresponding selection button(s). One or more of the operational modes may be implemented by other input systems described herein.

access the vasculature. The guide catheter, diagnostic catheter and guidewire are coaxial and inserted into the introducer sheath. To reduce risk of vessel injury, the EMDs are not inserted beyond the distal end of the introducer sheath. At this point, these EMDs are loaded into the robotic system, with the guide catheter in module 1, the diagnostic catheter in module 2 and the guidewire in module 3.

The interventionalist can observe the position of the EMDs in the body via fluoroscopic imaging. Using the input module, the EMDs are navigated up the femoral artery through the descending aorta to the aortic arch with the guidewire leading, as follows. Using the input system 100, the guidewire is selected as the active device and the analog trigger 172, a linear position control manipulated by the user's index finger, is used to instruct the system to advance the guidewire at a speed corresponding to the amount that the trigger is pulled. The advancing control could also be a scroll wheel which operates as a positional control, as described above and shown as element 154 in FIG. 13. Jog wheel 178 is manipulated rotationally by the user's right thumb to direct the angled tip of the wire along the correct path, and not into any side branching vessels. With the guidewire setting the path, the diagnostic and guide catheters are selected by activating devices 1 and 2, using the left thumb to depress 140E and 140F in series. Control 170 may then be depressed to advance the diagnostic and guide catheters along the guidewire to the base of the arch.

In the aortic arch, the guidewire and diagnostic catheter are manipulated sequentially or at the same time to direct the tip of the EMDs into the desired internal carotid artery branching off of the aortic arch. This might require the interventionalist to rotate and push the guidewire at the same time to get the tip in the right location, which can be accomplished by simultaneously manipulating jog wheel 178 with the right thumb along with one of either 184 or 172 linear controls with the right index finger. With the vessel selected, the guidewire can be advanced linearly, using rotation control as needed to stay on the desired path.

Once the guidewire has moved several inches up into the internal carotid artery, the diagnostic catheter and guide catheter can follow. This may be done by selecting both the diagnostic catheter and guide catheter as the active devices by pressing device selection control buttons 140E and 140F in series, and manipulating, with the left index finger, analog trigger 170 to instruct drive modules 1 and 2 to linearly move their respective EMDs simultaneously. With the guide

| Operational Mode | Controls 170/182 | Buttons 140E-140H | Control 176 | Controls 172/184 | Buttons 140A-140D | Control 178 |
|---|---|---|---|---|---|---|
| Single EMD | not used | Module 1-4 selection | not used | Linear motion of selected module | not used | Rotation of selected module |
| Two EMDs | Linear motion of catheter | Module 1-3 selection | Selected catheter rotation | Linear motion of wire | no selection required - wire selected | Rotation of wire |
| 1-device mode | not used | not used | Rotation of selected | Linear motion of selected | Module 1-4 selection | not used |
| 2-device mode | Linear motion of secondary | Module 1-3 secondary selection | not used | Linear motion of primary | Module 1-4 primary selection | not used |

Below, an example endovascular treatment of acute ischemic stroke using combined technique (i.e., using a stent retriever with aspiration) is described using the handheld input system 100 shown in FIG. 14. The introducer sheath is manually inserted into the femoral artery, giving a passageway for all other interventional devices (EMDs) to catheter in the internal carotid artery, the diagnostic catheter and guidewire are removed by using index fingers to manipulate control 184 to retract the wire, pressing 140F to select the diagnostic catheter and then pressing control 182 with the left index finger to retract the selected catheter, until both are safely within the guide catheter. At that point, the bedside operator can remove the diagnostic catheter and guidewire from the system manually. An aspiration catheter, microcatheter and microwire are then inserted into the guide catheter and then loaded in device modules 2, 3 and 4, respectively.

Control is assumed again by the interventionalist, who may simultaneously select to drive the aspiration catheter and microcatheter in modules 2 and 3 respectively by pressing 140F and 140G in series with the left thumb and holding button 140H to activate high speed travel mode for the analog trigger 170. The microwire is advanced by pulling trigger 172 with the right index finger. High speed travel mode may be used if devices are traveling within another catheter. The user releases button 140H to return to normal speed travel mode before the devices reach the tip of the catheter in which they are traveling.

In some instances, where tortuosity is encountered, the interventionalist may simultaneously select multiple catheters using some combination of 140E, 140F and 140G pressed in series and commanding them to retract using control 182, which has the effect of straightening bends in the vasculature for easier passage. In this case, the interventionalist may desire simultaneous and independent control of the microwire, such that the position of the microwire can actively be compensated as the catheters are retracted to ensure that the microwire's placement is not lost in a specific vascular branch or that the microwire does not advance to an unsafe location. The microwire linear position is controlled by controls 172 and 184, which can be manipulated by the right index finger simultaneously and independent from controls 170 and 182, which are manipulated by the left index finger to control linear motion of the selected catheters.

Once the target lesion is reached, the microwire and microcatheter are advanced through the clot. The microwire is retracted robotically inside the microcatheter, and then can be removed from the system. A stent retriever inserted into the microcatheter and its proximal end is loaded into device module 4. The system detects the presence of the stent retriever device in device module 4 using techniques as described above and the system maps control of device module 4 to the right side of the input module, to be manipulated using the controls 178, 184 and 172. The stent retriever is advanced using 172 to properly position the stent retriever relative to the clot. The interventionalist deploys the stent retriever by selecting the microcatheter by pressing 140G and slowly retracting it by manipulating button 182 while simultaneously slightly compensating with the linear wire controls 184 and 172 (which instructs device module 4 holding the stent retriever) to keep the stent retriever in place while the microcatheter is retracted into the aspiration catheter. The aspiration catheter is advanced to the face of the clot by pressing 140F and advancing using trigger 170. Tubing is connected to the hub of the aspiration catheter so that vacuum can be applied to the aspiration catheter. The stent retriever and the aspiration catheter are now retracted together, by selecting the aspiration catheter by pressing 140F and simultaneously pressing controls 182 and 184 to retract the aspiration catheter and the stent retriever respectively. The aspiration catheter and the stent retriever are retracted robotically into the guide catheter, and then can be unloaded from the system and fully retracted manually.

Figure 15:
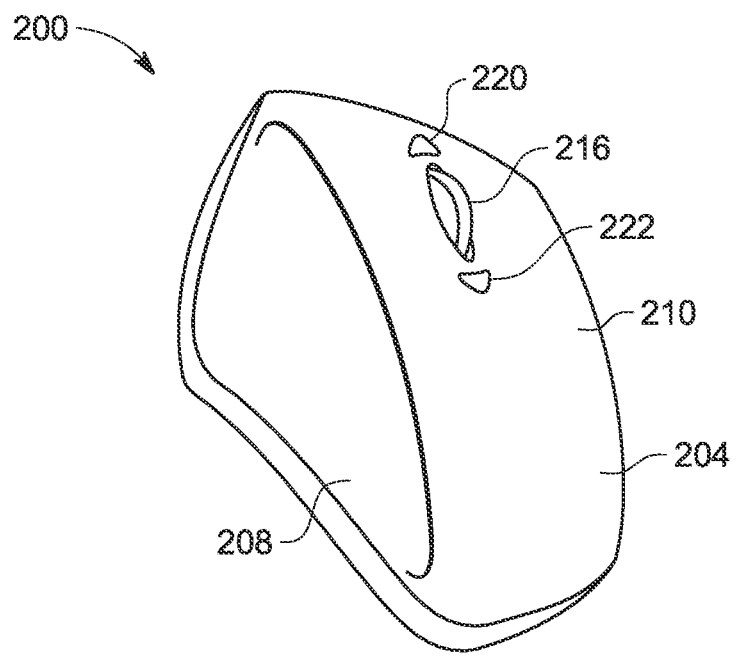
FIG. 15 is a perspective view of an input system including a scroll wheel in accordance with an embodiment.

In some embodiments, a catheter-based procedure system 10 can include at least one other input system. For example, FIG. 15 illustrates a perspective view of a handheld scrolling input system 200 for controlling a catheter-based procedure system 10 to perform a catheter based medical procedure in accordance with an exemplary embodiment. The scrolling input system 200 includes a body 204 configured to be grasped by the hand of a user so that the user's thumb can rest on a side surface 208 and the user's index finger and middle finger can rest on a top surface 210. The illustrated scrolling input system 200 has a generally flat bottom surface and is configured to rest on a surface while held by the user. In some embodiments, however, a scrolling input system can be configured to be held by a user without resting on any supporting surface.

A scrolling input control, such as the scroll wheel 216, can be positioned on the top surface 210 of the scrolling input system 200 proximate a front side of the body 204 so that it may be manipulated by the user's index finger or middle finger. Similar to other scroll wheels illustrated in FIGS. 7 and 13, the scroll wheel 216 can be positioned partially within the body 204 in a vertical orientation. One part of the scroll wheel 216 can be positioned within the body 204 so that it is inaccessible, while a different part of the scroll wheel 216 is accessible to the user and projects away from the top surface 210. Additionally, the scroll wheel 216 can be oriented so that its axis of rotation extends laterally from a left side of the body 204 to a right side, and is generally perpendicular to a median plane of the scrolling input system 200. Using their index finger or middle finger, a user can rotate the scroll wheel in a forward direction so that a point on the exposed section of the scroll wheel 216 moves towards the front side of the body 204, or in a backwards direction so that the point on the exposed section of the scroll wheel 216 moves towards the back side of the body 204. In some embodiments, the scroll wheel 216 can include detents that create discrete rotational position for the scroll wheel 216, and which may provide tactile feedback to the user.

Similar to the scrolling input controls described in connection to the handheld input system 100 of FIGS. 4-14, the scroll wheel 216 can be configured as a motion control that may be configured in a speed control mode or a position control mode, and can be used instruct the robotic drive 24 to move or rotate an EMD. For example, the scroll wheel 216 of the scrolling input system 200 can be configured to command axial movement of a selected EMD in a position control mode. In some embodiments, the user can instruct the robotic drive 24 to move the EMD in a distal direction by rotating the scroll wheel 216 towards the front side of the scrolling input system 200, and rotating the scroll wheel 216 towards the back side of the scrolling input system 200 can instruct the robotic drive to move the EMD in a proximal direction. As with the previously described scrolling input controls, the scroll wheel 216 can be configured to instruct the robotic drive to move or rotate an EMD by a prescribed increment each time the scroll wheel 216 is rotated a nominal angular distance, which may correspond to the angular distance between the discrete rotational positions created by the detents. Further, the relationship between the rotation of the scroll wheel 216 and rotation of the EMD may be scaled up or down (increasing or decreasing the amount of commanded rotation of the EMD) by the control computing system 34, or by the user.

Additionally or alternatively, a scrolling input system can include binary buttons that may be configured to move or rotate an EMD in a position or speed control mode, or to alter to operation of other input controls. In FIG. 15, for example, the scrolling input system 200 can include two binary buttons 220, 222 positioned on the top surface 210 so that they can be manipulated by the user's index finger or middle finger. The illustrated binary buttons 220, 222 are positioned proximate the scroll wheel 216, with a first binary button being position in front of the scroll wheel 216 and a second binary button 222 being arranged behind the scroll wheel 216. In other embodiments, however, a scrolling input system can include at least one binary input control in a different location.

In some control modes, the binary buttons 220, 222 can be configured as motion controls for controlling axial movement of the EMD in a speed control mode. In this configuration, the user may instruct the robotic drive 24 to continuously move the EMD in the distal direction at a prescribed rate by holding the first binary button 220, while holding the second binary button 222 may instruct the robotic drive 24 to continuously move the EMD in the proximal direction. Alternatively, the binary buttons 220, 222 may be configured as scaling inputs that can be pressed by a user to adjust the relationship between rotation of the EMD and rotation of the scroll wheel 216. Some embodiments of the scrolling input system 200 can include a mode-switching binary button (not shown) configured to switch the scroll wheel 216 into a continuous motion mode. While the binary button is held by the user, rotating the scroll wheel 216 forwards or backwards can instruct the robotic drive 24 to continuously move the EMD in the respective axial direction without repeated rotation of the scroll wheel 216. In some embodiments, repeated rotation of the scroll wheel 216 in may instruct the robotic drive to increase the axial movement speed of the EMD. Once the mode-switching binary button is released, the robotic drive 24 can stop moving the EMD and the scroll wheel 216 may return to a position control mode.

Figure 16:
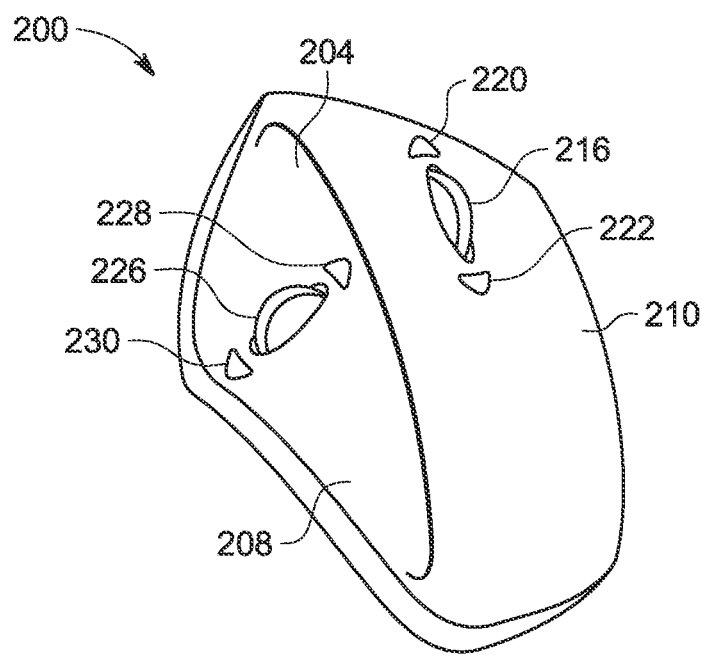
FIG. 16 is a perspective view of an input system including two scroll wheels in accordance with an embodiment.

In some embodiments a scrolling input system can include at least one additional input control for controlling a second degree of freedom of an EMD. For example, FIG. 16 illustrates a perspective view of a scrolling input system 200 that includes a secondary scroll wheel 226 and two additional binary buttons 228, 230 positioned on the side surface 208. The secondary scroll wheel 226 can be positioned partially within body 204 and may have an axis of rotation that generally extends from the front side of the scrolling input system 200 to the back side. Thus, using their thumb, the user can rotate the secondary scroll wheel 226 in an upward direction (clockwise when viewed from behind) or in a downward direction (counterclockwise when viewed from behind).

When used in some control modes, the secondary scroll wheel 226 can be configured in a position control mode for commanding rotational motion of the selected EMD. For example, rotating the secondary scroll wheel 226 in the clockwise direction may instruct the robotic drive 224 to rotate the EMD in a clockwise direction, while counterclockwise rotation of the secondary scroll wheel 226 may instruct the robotic drive 24 to rotate the EMD in the counterclockwise direction. Thus, using a scrolling input system with two scroll wheel 216, 226, a user can simultaneously and independently control two degrees of freedom of an EMD with scrolling input controls. Similar to the first scroll wheel 216, the relationship between rotation of the secondary scroll wheel 226 and the commanded movement of the EMD may be configurable. In some modes, there may be a 1:1 relationship between angular motion of the EMD and rotation of the secondary scroll wheel 226. In such an embodiment, the robotic drive 24 will rotate the EMD the same angular distance that the secondary scroll wheel 226 was rotated by the user. In other embodiments, however, the robotic drive 24 can be configured to rotate the EMD more or less than the secondary scroll wheel 226 is rotated by the user.

The third binary button 228 and the fourth binary button 230, which are respectively positioned above and below the secondary scroll wheel 226 in the illustrated embodiment, can be configured to be pressed by the thumb of the user, and may be configured to function similarly to the binary buttons 220, 222 on the top surface 210. For example, the third and fourth binary buttons 228, 230 can be configured in a speed control mode, and can respectively command rotation of the EMD in the clockwise and counterclockwise directions when held by the user. Alternatively, the third and fourth binary buttons 228, 230 can be configured as scaling inputs for adjusting the relationship between rotation of the secondary scroll wheel 226 and commanded rotation of the EMD.

Figure 17:
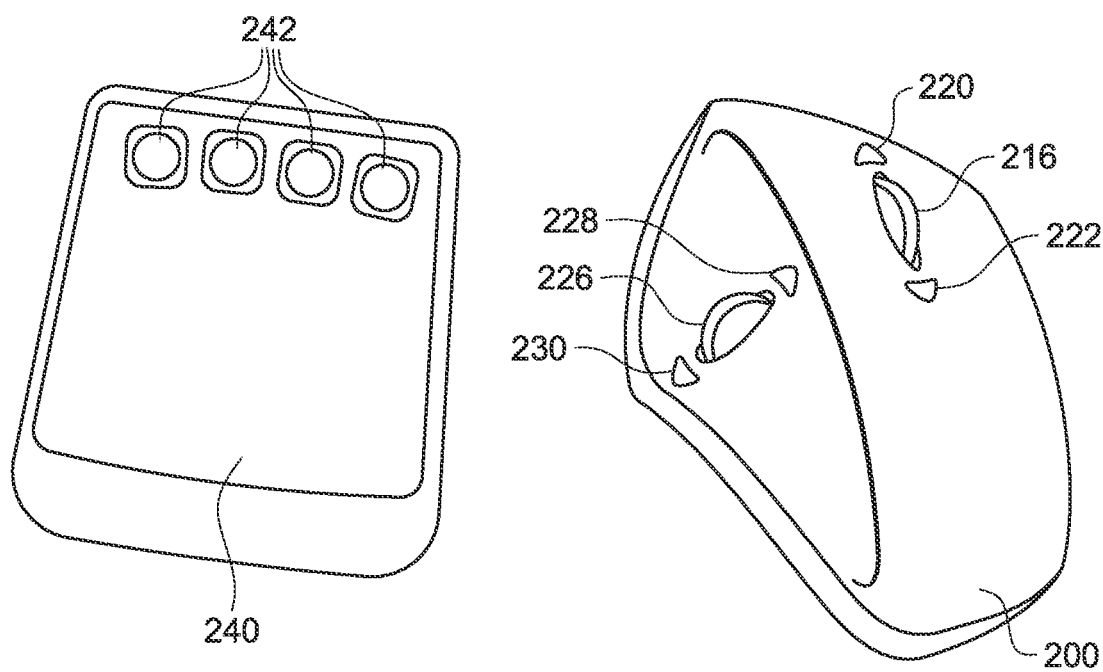
FIG. 17 is a perspective view of the input system of FIG. 16 with a button pad in accordance with an embodiment.

In some embodiments, a catheter-based procedure system 10 can include at least one additional input system configured to be used with a scrolling input system. As illustrated in FIG. 17, for example, a button pad 240 can include multiple input controls, such as binary buttons 242, that may be manipulated using a second hand of a user while their first hand operates the scrolling input system 200. Each of the binary buttons can be configured as selection controls for selecting which of the EMDs and/or device modules 32 will be controlled by the scrolling input system 200. In some embodiments, the binary buttons 242 can be configured as selection controls in a continuous activation selection mode. While the user presses at least one of the binary buttons 242, axial and rotational motion of EMDs and/or device modules 32 that correspond to the pressed selection controls can be controlled using the input controls of the scrolling input system 200. However, if the user tries to move an EMD or device module 32 module without holding the selection control, the robotic drive 24 would not move any devices. Additionally, the robotic drive 24 will stop moving a device if the user releases the corresponding selection control. In other embodiments, at least one selection control can be configured in a toggling selection mode in which a selection control does not need to be held by a user.

Figure 24:
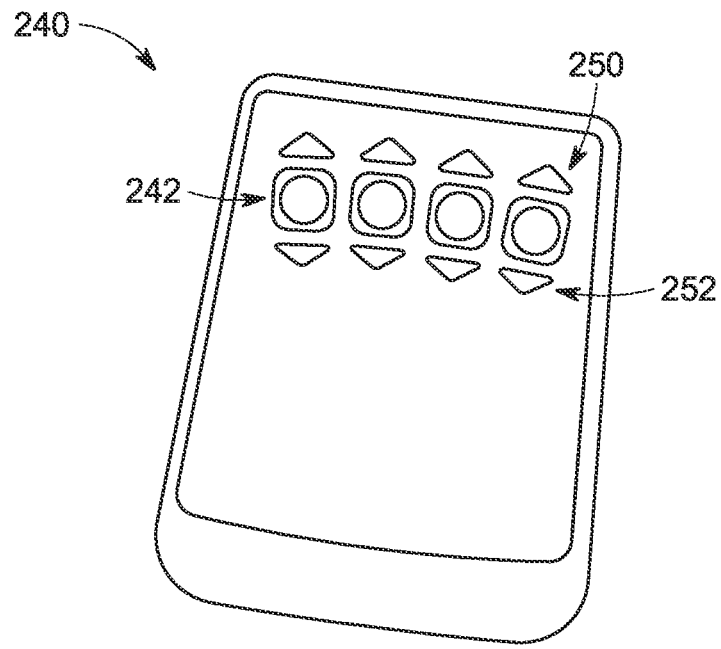
FIG. 24 is a perspective view of a button pad including binary motion controls in accordance with an embodiment.

Some button pads can include at least one additional binary, analog, and/or scrolling input control configured to control axial motion or rotation of at least one EMD. FIG. 24 illustrates an embodiment of a button pad 240 that includes a plurality of first binary motion controls 250 arranged above the binary buttons 242 (which are configured as selection controls), and a plurality of second binary motion controls 252 arranged below the binary buttons. Each of the first and second binary motion controls 250, 252 can be configured to control axial or rotational motion of an EMD corresponding to the binary button 242 that a particular binary motion control 250, 252 is positioned above or below. For example, the first binary motion controls 250 can be configured to command the robotic drive 24 to move or rotate a corresponding EMD in a first direction when held by the user, while the second binary motion controls 252 can command the robotic drive 24 to move or rotate the corresponding EMD in a second direction. Using one hand, the user can simultaneously hold at least one selection control 242 and at least one binary motion control 250, 252. Using the other hand at the same time, the user can manipulate a scroll wheel 216, 226 and/or press one of the binary buttons 220, 222, 228, 230 on the scrolling input system 200. Thus, a user can control motion of at least one EMD by holding a corresponding one binary motion control 250, 252 while simultaneously controlling movement of the selected EMD(s) using the scrolling input system 200.

Figure 25:
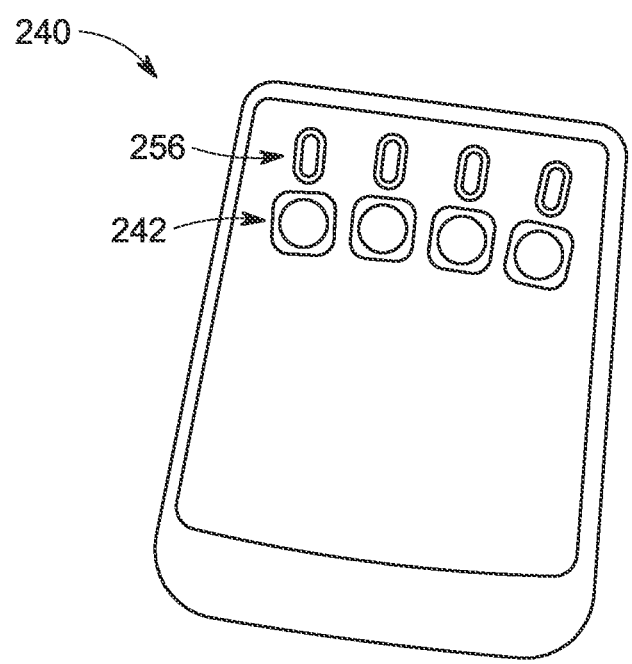
FIG. 25 is a perspective view of a button pad including scrolling motion controls in accordance with an embodiment.

In a similar embodiment illustrated in FIG. 25, an embodiment of a button pad 240 that includes a plurality of scrolling motion controls 256 arranged above, and corresponding to, one the binary buttons 242 configured as selection controls. As with the binary motion control 250, 252, a user can manipulate the scrolling motion controls 256 to control axial or rotational motion of an EMD while simultaneously controlling motion of another EMD with the scrolling input system 200. Further, a user can use a button pad 240 to command the robotic drive 24 to move or rotate an EMD without simultaneous use of a scrolling input system 200. For example, the user can use one or both hands to manipulate the binary motion control 250, 252 of FIG. 24 or the scrolling motion controls 256 of FIG. 25 to control movement of multiple EMDs.

Figure 18:
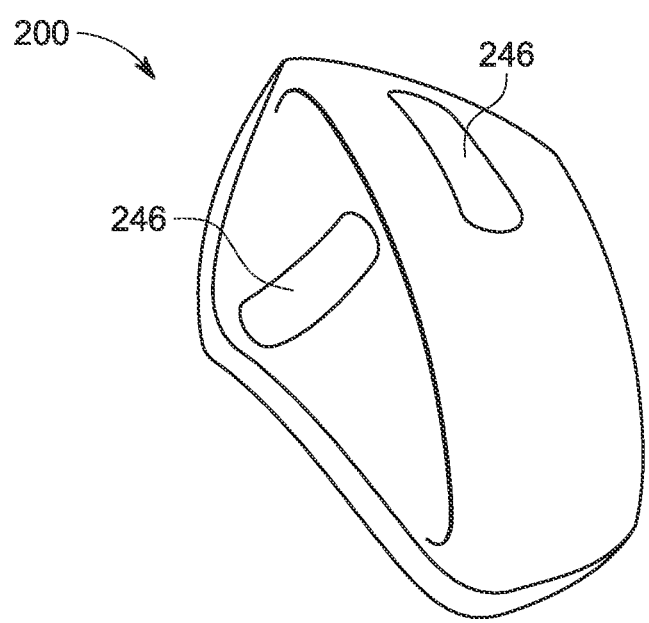
FIG. 18 is a perspective view of an input system including two touch input controls in accordance with an embodiment.

In some embodiments, a scrolling input system can include alternative input control configurations. For example, FIG. 18 illustrates a scrolling input system 200 that uses two touch input controls 246 in place of the two scroll wheels 216, 226 of FIGS. 17 and 18. A user may slide a finger along the touch input controls 246, which may be configured as capacitive touch pads, in order to simulate a scrolling input control. In another embodiment, at least one of the scroll wheels 216, 226 may be omitted and binary buttons may be provided to control axial or rotational motion of the EMD. Some embodiments of a catheter-based procedure system may include at least on additional button pad and/or at least one additional scrolling input control, which may be different or the same as the illustrated embodiments. Further, although the scrolling input systems illustrated in FIGS. 15-19 are configured to be grasped by the user's right hand, it should be appreciated that similar scrolling input systems can include a body that is configured to be grasped by a user's left hand.

Figure 19:
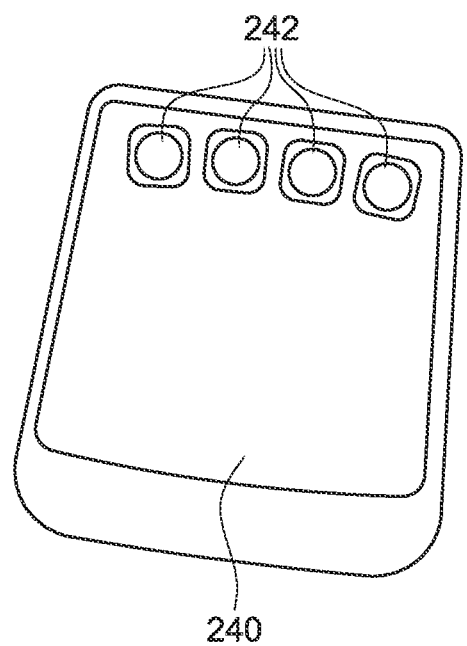
FIG. 19 is a perspective view of a translating input system and a button pad in accordance with an embodiment.
Figure 19:
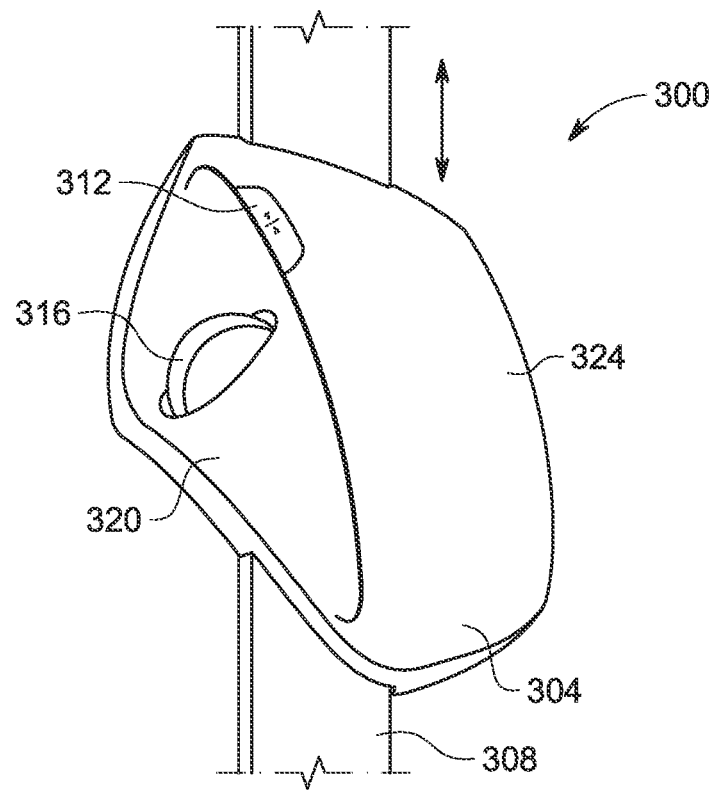

FIG. 19 illustrates a perspective view of a translating input system 300, as well as a button pad 240, that can be used to control the robotic drive 24 based on linear movement of the translating input system 300. The translating input system 300 includes a body 304 that is configured to slide along a guide rail 308, and which can be held in one of the user's hands. The illustrated guide rail 308 constrains movement of the translating input system 300 to a single axis, thereby limiting its movement to a forward direction (away from the user) and a backwards direction (towards the user). Other embodiments may be constrained in different directions. For example, a translating input system may be configured to slide on a rail that constrains the translating input system to lateral (left and right) motion relative to the user. In another embodiment, the movement of a translating input system may be physically unconstrained so that it can be moved in any direction. An unconstrained translating input system can be configured to control axial and rotational motion of an EMD based on its movement along two perpendicular axes. Alternatively, an unconstrained translating input system can be configured to only measure movement along one axis, or the control computing system 34 may be configured to only interpret movement of the translating input system along a single axis.

With continued reference to FIG. 19, the translating input system 300 can be configured instruct the robotic drive 24 to move or rotate an EMD based on its movement along the rail 308. For example, the translating input system 300 can be configured to control axial movement of a selected EMD in a position control mode. When in a position control mode, the translating input system 300 can instruct the robotic drive 24 to move the EMD by a prescribed increment each time the translating input system 300 moves a nominal linear distance. The direction of the commanded EMD movement can be based on which direction the user moves the translating input system 300. Thus, in some embodiments, a user can instruct the robotic drive 24 to move the EMD in the distal direction by moving the translating input system 300 in the forward direction, or in the proximal direction by moving the translating input system in the backwards direction.

The range of linear the movement for the translating input system 300 may be constrained by various different boundaries, for example, a stop member defining an end of the rail 308, the size of, or available space at, the control station, the physical reach of the user, or any other limiting factor or structure. In order to continue moving the translating input system 300 once a limit has been reached, translating input system 300 must be moved back towards the opposite end of its range of motion without actuating commanding movement of the EMD. In some embodiments, a user may be able to lift the translating input system 300 up off of the surface on which it slides. In such an embodiment, the user can lift up the translating input system, move it back towards the other end of its range of motion, and place it back down without instructing the robotic drive 24 to move the EMD.

Additionally or alternatively, some embodiments of the translating input system 300 can include a continuous activation button 312 that the user must hold in order to control axial or rotational motion of the EMD. While the continuous activation button 312 is not being pressed by the user, the robotic drive 24 will not move the selected EMD in response to movement of the translating input system 300. In addition to helping to prevent incidental axial and rotational movement of the EMD, the continuous activation button 312 allows the user to return the translating input system 300 to its operable range by simply moving it while the button 312 is not pressed.

Similar to the previously discussed scrolling input controls, the relationship between how for the user moves the translating input system 300 and how far the robotic drive 24 moves the EMD can be configurable or fixed. Some embodiments may include at least one scaling input on the translating input system 300 or the button pad that can be used to increase or decrease the how far the robotic drive 24 moves the EMD when the translating input system 300 is moved any given distance. Further, the control computing system 34 may adjust the ratio of commanded EMD motion to movement of the translating input system 300 based on which EMD and/or device module 32 is selected, or based on other system parameters.

In some embodiments, the body 304 of the translating input system 300 may be similar to that of a scrolling input system illustrated in any of FIGS. 15-18. A side surface 320 of the translating input system 300 can include a scroll wheel 316, which can be in a similar or the same position as the secondary scroll wheel 226 in FIGS. 16 and 17. The scroll wheel 316 can be configured as a motion control that may allow the user to control rotational motion of the EMD while axial movement is simultaneously controlled by sliding the translating input system 300. Additionally or alternatively, some translating input systems can include at least one other input control positioned on the top surface 324 of the translating input system 300, the side surface, or at any other location. Further, the translating input system 300 can be used in conjunction with a button pad 240 that includes multiple binary buttons 242 that may be manipulated by the user to adjust the motion commands produced using the translating input system 300. For example, as with the button pad of FIG. 17, the binary buttons 242 can be configured as selection controls for selecting which of the EMDs and/or device modules 32 will be controlled using the translating input system 300.

Figure 20:
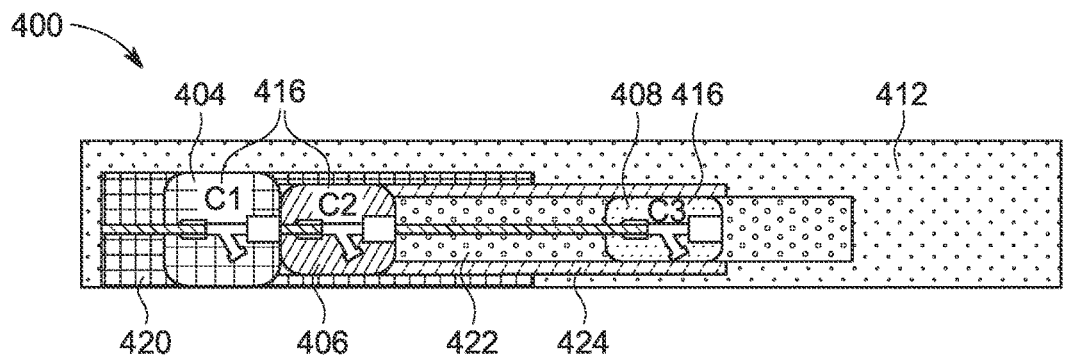
FIG. 20 is a graphical user interface displaying position information in accordance with an embodiment.
Figure 21:
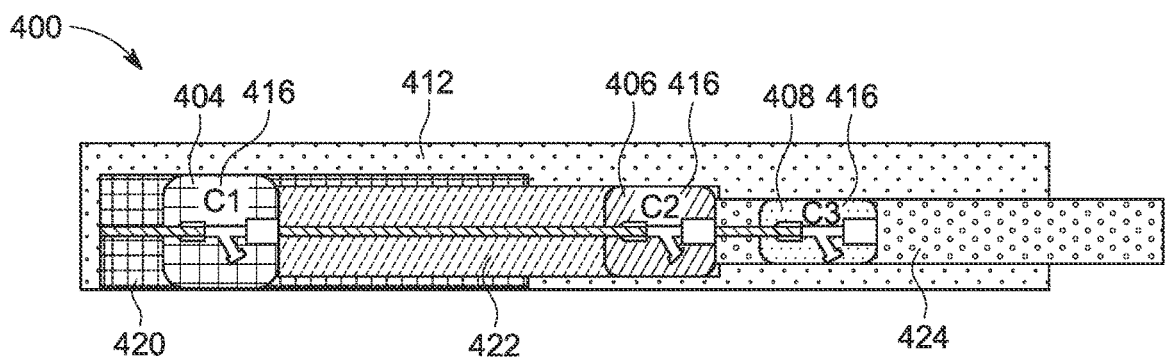
FIG. 21 is a graphical user interface displaying position information in accordance with an embodiment.

In some embodiments, the control station 26 can include a user interface configured to provide a user with feedback and information regarding the state of the catheter-based procedure system 10. For example, the display 30 can provide a graphical user interface (GUI) that illustrates the positions and travel limits of the device modules 32 of a robotic drive 24. FIGS. 20 and 21 illustrate embodiments of a GUI 400 configure to provide position information for a robotic drive 24 with three device modules 32, which are denoted with the labels "C1," "C2," and "C3." The three devices modules 32 are each represented by an icon 404, 406, 408 that is arranged linearly within a boundary region 412 that represents the total length of the robotic drive 24. To help the user to determine which icon 404, 406, 408 corresponds to each of the device modules 32, each of the icons can include a text label 416 that denotes which devices module 32 the icon 404, 406, 408 represents. Additionally, the icons 404, 406, 408 can be vividly colored or have different fill patterns to help a user to differentiate between each of the icons 404, 406, 408. The position of each icon 404, 406, 408 corresponds to the position of the corresponding device module 32 on the robotic drive 24. In the illustrated embodiments, the left side if the boundary region 412 represents the distal end of the robotic drive 24 while the right side represents the proximal end of the robotic drive 24. In other embodiments, however, a GUI can be configured in other orientations.

The GUI 400 can also include range bars 420, 422, 424 that illustrate the travel ranges of each of the device modules 32. Each of the range bars 420, 422, 424 can have a color, fill pattern, or other design feature that corresponds to the design of the corresponding one of the icons 404, 406, 408. For example, the range bars 420, 422, 424 can each be filled with a lighter shade of the color used for the corresponding icons 404, 406, 408. To illustrate overlapping travel ranges, the range bars 420, 422, 424 can have different widths so that they appear to be layered on top of each other. For example, the range bar 420 of the first device module 32 (represented by the leftmost icon 404) appears to be behind the range bar 422 of the second device module 32 (represented by the middle icon 406).

In the illustrated embodiments, the distal travel limit for each device module 32 is defined by the position of the device module 32 in front of it (in the distal direction), or by the distal end of the robotic drive 24. Thus, the range bar 420 of the first device module 32 is attached to the left side of the boundary region 412, while the range bars 422, 424 of the second and third device modules 32 (represented by the middle icon 406 and rightmost icon 408, respectively) are attached to the right side (proximal end) of the adjacent device module 32 in the distal direction. The proximal travel limit for each device module 32 is defined by a system-implemented limit (which may be defined by the user or by the system) as well as the position of the device module 32 behind it (in the proximal direction), or by a limit defined by the user or by the system. Thus, the right side of each of the range bars 420, 422, 424 (representing the proximal travel limits) is spaced apart from the left side by a distance that corresponds to the distance between the distal travel limit and the system-defined proximal travel limit. However, because the distal travel limit of the device modules 32 is defined by the proximal side of the adjacent device module 32, each device module 32 can be moved inside of the travel range of the distally-adjacent device module 32. In FIG. 20, for example, the range bar 424 of the third device module 32 (which is represented by the rightmost icon 408) overlaps with the range bar 422 of the second device module 32.

As illustrated in FIG. 21, the maximum travel range of a device module (in this case, the range bar 424 of the third device module 32) may be illustrated as extending outside of the boundary region 412. Although the proximal travel limit of the third device module in this case is the proximal end of the robotic drive 24, this may be useful in order to show that the maximum travel range of the third device module 32 is longer than the distance between the proximal end of the second device module 32 and the proximal end of the robotic drive. In some embodiments, the GUI 400 can be configured to display additional graphics or text when a device module 32 reaches a travel limit. The additional graphics or text may indicate where the limit, what is defining the travel limit, and how the user can control the robotic drive 24 to continue moving the device module 32. Further, the GUI 400 may highlight or otherwise point out the "contact point" between device modules 32 on the graphical illustration of their positions. In addition to displaying the proximal end of EMDs (as shown in FIG. 20 and FIG. 21), in one embodiment the distal tip of EMDs can be displayed (not shown). This may be helpful to drive an EMD inside another EMD without use of fluoroscopy. Additionally, GUI 400 may communicate the device presence or absence, the cassette presence or absence, and notifications such as encoder mismatch, encoder issues, transducer issues, and any other notifications.

While the illustrated GUI 400 is shown in a configuration for a catheter-based procedure system 10 with three device modules, other embodiments can be used with a catheter-based procedure system that includes more than three or fewer than three device modules. Depending on the configuration of the robotic drive 24 a GUI can change to display the appropriate number of device modules and their travel ranges. GUI 400 may also include numeric readout of device module position, which could be in reference to its absolute position along the full range of the system, or its remaining travel distance in either direction. Further, GUI 400 can be configured to indicate which of the device modules 32 have been selected by the user. For example, the icons 404, 406, 408 can be configured to switch between a selected state indicating that the user has selected that corresponding device module 32 using the input system 28, and an unselected state indicating that the device module 32 has not be selected (and therefore will not be controlled using the motion controls).

In some embodiments, a GUI may also provide a graphical representation of the input system 28 and the input controls on input system (for example, the buttons, knobs, joysticks, or any other input controls) using an input map (not illustrated). As the input controls are manipulated by the user, the button map can indicate which input controls are being activated. This may be useful so that the user may see which input controls are being manipulated without looking at the input system 28. For example, the button map can include an array of icons corresponding to each or the input controls, which may be arranged on screen in a pattern that is similar to the physical arrangement of the input controls on the input system 28. Each icon can be configured to light up and/or be animated when manipulated by the user. For binary input controls, corresponding icon on the button map may indicate whether the input control is in an activated (pressed) or inactivate (unpressed) state. The icons corresponding to analog input controls may indicate a degree of manipulation.

Figure 22:
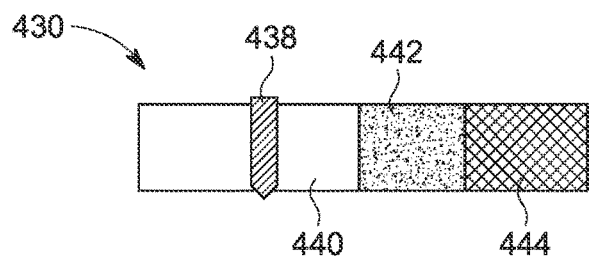
FIG. 22 is a graphical user interface displaying load information via a linear gauge in accordance with an embodiment.
Figure 23:
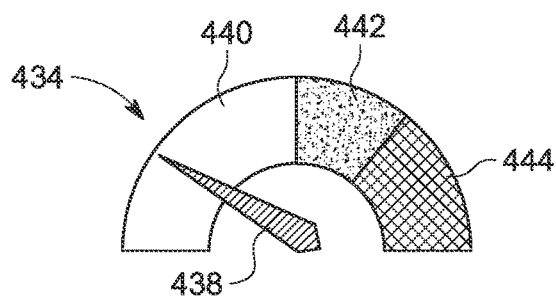
FIG. 23 is a graphical user interface displaying load information via a rotary gauge in accordance with an embodiment.

In some embodiments, a GUI can be configured to provide a graphical representation of different forces and/or torques that are acting on an EMD or a device module 32. For example, FIG. 22 illustrates a linear gauge 430 configured to show a measured load, and FIG. 23 illustrates a rotary gauge 434 for illustrating a measured load. Each gauge 430, 434 includes a pointer 438 configured to point to a position on the gauge 430, 434 corresponding the amount of force or torque acting on the EMD or device module 32. Multiple different zones 440, 442, 444 can be marked along the gauges 430, 434, each corresponding to different load thresholds. The zones 440, 442, 444 can have different colors and/or fill patterns in order to help the user to differentiate between zones. In other embodiments, a GUI can include a load gauge in a different shape, size, or configuration. Further, a GUI can include a load gauge that does not include distinct zone designations. In another embodiment the graphical representations of measured loads are applied to and integrated with the robotic drive user interface shown in FIG. 20 and FIG. 21.

Along with a graphical representation, the GUI can include a numeric readout of the measured load. Further, the measured force or torque may be communicated by changes in color shade and/or intensity. A light can be configured to change between discrete colors and intensities as different load thresholds are passed, or it may be configured to gradually change or fade between different colors and intensities. For example, a numeric readout of a measured load can be configured to fade from a first color associated with a minimum or no measured load, to a second color associated with a maximum load limit. Additionally or alternatively, a load indicator light, which may be shown on the display 30, the input system 28, or any other location on the control station 26, may change color based on the measured load. The value of the different load thresholds, including the maximum load limit, may be constant or they can be programmable and adjustable by user to accommodate different limits. This may be useful, for example, so that different users can set different limits based on their personal preference. Further, the control computing system 34 can be configured to prevent the user from exceeding the maximum load limit. Alternatively, the maximum load limit may be displayed on the display 30, but the user may be able to override it.

In addition to visual feedback, the control station 26 may be configured to provide physical feedback to the user. For example, feedback may be provided in the form of at least one of vibration, cogging, and a resistance or counteracting force. In some embodiments, vibration feedback may be used to provide various alerts. The vibrations may be provided at on preset, constant intensity, or the intensity may vary based of different levels of the alerts. For example, the intensity of vibrations may increase as a measured load approaches a maximum load limit. Alternatively, different intensities or vibration patterns may be to differentiate between different alerts. Cogging feedback refers to the sensation of incremental bumps or clicks that give the user a sensation of a control mechanism traveling. In some embodiments, this may be similar to the tactile feedback provided by a scrolling input control as it is rotated between positions created by its detents. Some systems, however, can use at least one different sensation for cogging feedback. The type and intensity of the cogging sensation may be fixed, or it may be adjustable by the user or by the system.

Physical feedback may be by physical interactions between components that occur as the user manipulates the input system 28, or it can be simulated using electromechanical devices. For example, a motor can be controlled to provide a tapping sensation as cogging feedback. When physical feedback is provided through an input system 28, the feedback may be felt throughout the input system, it may be provided near (or appear to originate from) an area located close to specific input controls. For example, vibration feedback can be provided by a motor (or any other device) that is near an input control to indicate alerts associated with that input control.

In some embodiments, input controls configured a motion controls be configured to provide physical feedback associated with a force or torque measured on the EMD or device module 32 being controlled by the input control. An analog trigger, a scroll wheel, a slider, or a translating input system may include a braking mechanism configured to resist manipulation by the user. In some embodiments the braking force may be provided by a passive system, such as a dampening system. Other embodiments can include a motor configured to apply a counteracting force to resist manipulation of the input control by the user. The strength of the counteracting force may be adjustable by the system or by the user and can vary based on a load measured by the system.

Computer-executable instructions for controlling a catheter-based procedure system according to methods using any of the above-described components may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

The patentable scope herein is defined by the claims, and may include other examples that occur to those in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the embodiments described herein without departing from the spirit thereof. The scope of these and other changes will become apparent from the appended claims.

We claim:

1. An input system for controlling a catheter-based procedure system that includes a robotic drive, the input system comprising:
 a body comprising a top surface and a front surface and;
 a first control disposed on the front surface and configured to instruct the robotic drive to axially move a first elongated medical device in response to manipulation of the first control by a user; and
 a second control disposed on the top surface and configured to instruct the robotic drive to rotate the first elongated medical device in response to manipulation of the second control by the user, wherein the first control and the second control are disposed to allow manipulation of the first control by an index finger of the user and manipulation of the second control by a thumb of the user.

2. An input system according to claim 1, further comprising a third control coupled to the body, wherein the first control and the second control are configured to instruct the robotic drive only if the third control is manipulated by the user.

3. An input system according to claim 2, wherein the first control is configured to instruct the robotic drive to axially move the first elongated medical device at a constant speed in response to manipulation of the first control by a user, and
wherein the second control is configured to instruct the robotic drive to rotate the first elongated medical device by a discrete angle in response to manipulation of the second control by the user.

4. An input system according to claim 1, further comprising a third control coupled to the body and configured to map the first control and the second control to a second elongated medical device,
wherein mapping the first control and the second control to the second elongated medical device results in configuration of the first control to instruct the robotic drive to axially move the second elongated medical device in response to manipulation of the first control by the user, and configuration of the second control to instruct the robotic drive to rotate the second elongated medical device in response to manipulation of the second control by the user.

5. An input system according to claim 4, further comprising a fourth control coupled to the body, wherein the first control and the second control are configured to instruct the robotic drive only if the fourth control is manipulated by the user.

6. An input system according to claim 5, further comprising a fifth control coupled to the body and configured to map the third control and the fourth control to a third elongated medical device,
wherein mapping the third control and the fourth control to the third elongated medical device configures the third control to instruct the robotic drive to axially move the third elongated medical device in response to manipulation of the third control by the user and configures the fourth control to instruct the robotic drive to rotate the third elongated medical device in response to manipulation of the fourth control by the user.

7. An input system according to claim 1, further comprising a third control coupled to the body, wherein the first control and the second control are configured to instruct the robotic drive only if the third control is manipulated by the user.

8. An input system according to claim 1, wherein the first control is configured to instruct the robotic drive to axially move the first elongated medical device a continuous speed in response to manipulation of the first control by a user, and
wherein the second control is configured to instruct the robotic drive to rotate the first elongated medical device by a discrete angle in response to manipulation of the second control by the user.

9. An input system according to claim 1, further comprising:
a third control disposed on the front surface and configured to instruct the robotic drive to axially move a second elongated medical device in response to manipulation of the third control by a second index finger of a second hand of the user.

10. An input system according to claim 9, further comprising:
a fourth control coupled to the body and configured to map the first control and the second control to a selected one of two or more elongated medical devices; and
a fifth control coupled to the body and configured to map the third control to a second selected one of two or more elongated medical devices.

11. An input system according to claim 10, wherein the fourth control is configured to map the first control and the second control to the selected one of two or more elongated medical devices only while the fourth control is manipulated by the user, and
wherein the fifth control is configured to map the third control to the second selected one of two or more elongated medical devices only while the fifth control is manipulated by the user.

12. A method for an input system for controlling a catheter-based procedure system that includes a robotic drive, the method comprising:
receiving a first manipulation by an index finger of a first hand of a user of a first control coupled to a front surface of a body of the input system;
receiving a second manipulation by a thumb of the first hand of the user of a second control coupled to a top surface of the body of the input system;
responsive to the first manipulation, instructing the robotic drive to axially move a first elongated medical device; and
responsive to the second manipulation, instructing the robotic drive to rotate the first elongated medical device,
wherein the first manipulation and the second manipulation occur simultaneously.

13. A method for an input system according to claim 12, further comprising:
receiving a third manipulation of a third control coupled to the body, wherein the robotic drive is instructed only if the third manipulation is received simultaneously with the first manipulation and the second manipulation.

14. A method for an input system according to claim 13, wherein the first control is configured to instruct the robotic drive to axially move the first elongated medical device a continuous speed responsive to manipulation of the first control by a user, and
wherein the second control is configured to instruct the robotic drive to rotate the first elongated medical device by a discrete angle responsive to manipulation of the second control by the user.

15. A method for an input system according to claim 12, further comprising:
receiving a third manipulation of a third control coupled to the body; and
responsive to the third manipulation, mapping the first control and the second control to a second elongated medical device.

16. A method for an input system according to claim 15, further comprising receiving a fourth manipulation of a fourth control coupled to the body, wherein the robotic drive is instructed only if the fourth manipulation is received simultaneously with the first manipulation and the second manipulation.

17. A method for an input system according to claim 15, wherein the first control and the second control are mapped to the second elongated medical device only while the third control is manipulated by the user.

18. A method for an input system according to claim 12, further comprising:
   receiving a third manipulation by an index finger of a second hand of the user of a third control coupled to the front surface of the input system;
   receiving a fourth manipulation by a thumb of the second hand of the user of a fourth control coupled to the top surface of the input system;
   responsive to the third manipulation, instructing the robotic drive to axially move a second elongated medical device; and
   responsive to the fourth manipulation, instructing the robotic drive to rotate the second elongated medical device,
   wherein the third manipulation and the fourth manipulation occur simultaneously.

19. A method for an input system according to claim 12, wherein the first control is configured to instruct the robotic drive to axially move the first elongated medical device a continuous speed responsive to manipulation of the first control by a user, and
   wherein the second control is configured to instruct the robotic drive to rotate the first elongated medical device by a discrete angle responsive to manipulation of the second control by the user.

20. A method for an input system according to claim 12, further comprising:
   receiving a third manipulation of a third control coupled to the front surface of the body; and
   responsive to the third manipulation, instructing the robotic drive to axially move a second elongated medical device.

\* \* \* \* \*